United States Patent
Habener et al.

(10) Patent No.: US 9,040,481 B2
(45) Date of Patent: May 26, 2015

(54) METHODS FOR TREATING STEATOTIC DISEASE

(75) Inventors: Joel F. Habener, Newton Center, MA (US); Eva Tomas-Falco, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 13/882,825

(22) PCT Filed: Nov. 2, 2011

(86) PCT No.: PCT/US2011/058907
§ 371 (c)(1),
(2), (4) Date: Jul. 16, 2013

(87) PCT Pub. No.: WO2012/061466
PCT Pub. Date: May 10, 2012

(65) Prior Publication Data
US 2013/0288961 A1 Oct. 31, 2013

Related U.S. Application Data

(60) Provisional application No. 61/409,288, filed on Nov. 2, 2010, provisional application No. 61/416,128, filed on Nov. 22, 2010.

(51) Int. Cl.
| | |
|---|---|
| A61K 38/00 | (2006.01) |
| A61K 38/26 | (2006.01) |
| A61K 38/08 | (2006.01) |
| A61K 38/04 | (2006.01) |
| A61P 3/06 | (2006.01) |
| A61P 3/10 | (2006.01) |
| A61P 7/12 | (2006.01) |
| C07K 14/605 | (2006.01) |
| C07K 5/00 | (2006.01) |
| C07K 16/00 | (2006.01) |
| C07K 17/00 | (2006.01) |
| C07K 7/08 | (2006.01) |
| A61K 48/00 | (2006.01) |
| C07K 14/775 | (2006.01) |
| A61K 38/17 | (2006.01) |
| C07K 14/575 | (2006.01) |
| A61K 38/10 | (2006.01) |
| C07K 7/06 | (2006.01) |

(52) U.S. Cl.
CPC . C07K 7/08 (2013.01); A61K 38/26 (2013.01); A61K 48/00 (2013.01); C07K 14/605 (2013.01); C07K 14/775 (2013.01); A61K 38/1709 (2013.01); C07K 14/57563 (2013.01); A61K 38/08 (2013.01); A61K 38/10 (2013.01); C07K 7/06 (2013.01)

(58) Field of Classification Search
None
See application file for complete search history.

(56) References Cited

U.S. PATENT DOCUMENTS

| | | |
|---|---|---|
| 5,574,008 A | 11/1996 | Johnson et al. |
| 5,846,937 A | 12/1998 | Drucker |
| 6,268,343 B1 | 7/2001 | Knudsen et al. |
| 6,344,180 B1 | 2/2002 | Holst et al. |
| 6,395,767 B2 | 5/2002 | Robl et al. |
| 6,444,788 B1 | 9/2002 | Staby |
| 6,458,924 B2 | 10/2002 | Knudsen et al. |
| 6,528,486 B1 | 3/2003 | Larsen et al. |
| 6,573,287 B2 | 6/2003 | Sulsky et al. |
| 2001/0011071 A1 | 8/2001 | Knudsen et al. |
| 2001/0047084 A1 | 11/2001 | Knudsen et al. |
| 2002/0006899 A1 | 1/2002 | Pospisilik et al. |
| 2002/0019411 A1 | 2/2002 | Robl et al. |
| 2002/0110560 A1 | 8/2002 | Demuth et al. |
| 2002/0183367 A1 | 12/2002 | Sulsky et al. |
| 2003/0004095 A1 | 1/2003 | Reimer et al. |
| 2003/0073626 A1 | 4/2003 | Hathaway et al. |
| 2003/0091507 A1 | 5/2003 | Holst et al. |
| 2003/0176357 A1 | 9/2003 | Pospisilik et al. |
| 2003/0199451 A1 | 10/2003 | Mogensen et al. |
| 2003/0199672 A1 | 10/2003 | Knudsen et al. |
| 2003/0220243 A1 | 11/2003 | Glaesner et al. |
| 2003/0220274 A1 | 11/2003 | Oh et al. |
| 2003/0225102 A1 | 12/2003 | Sankaranarayanan |
| 2004/0266678 A1 | 12/2004 | Beeley et al. |
| 2006/0014241 A1 | 1/2006 | Glaesner et al. |
| 2006/0183682 A1 | 8/2006 | Juul-Mortensen |
| 2008/0194483 A1* | 8/2008 | Brownlee ........................ 514/12 |
| 2008/0300173 A1 | 12/2008 | DeFrees |
| 2009/0227519 A1 | 9/2009 | Balasubramaniam |
| 2010/0184645 A1 | 7/2010 | Verdine et al. |
| 2010/0286024 A1* | 11/2010 | Kanda ............................ 514/1.9 |

FOREIGN PATENT DOCUMENTS

| | | |
|---|---|---|
| EP | 0708179 A2 | 10/1995 |
| EP | 0699686 A2 | 3/1996 |
| EP | 1076066 | 2/2001 |

(Continued)

OTHER PUBLICATIONS

Fodor et al., "Recommendations for the management and treatment of dyslipidemia," Can. Med. Assoc. J. 162:1441-7 (2000).*
Green et al., "Degradation, receptor binding, insulin secreting and antihyperglycaemic actions of palmitate-derivatised native and Ala8-substituted GLP-1 analogues," Biol. Chem. 385:169-177 (2004).*
Knudsen, et al., "Potent Derivatives of GLucagon-like Peptide-1 with Pharmacokinetic Properties Suitable for Once Daily Administration," J. Med. Chem. 43:1664-1669 (2000).*
U.S. Appl. No. 14/128,801, filed Dec. 2013, Habener, Joel.*

(Continued)

*Primary Examiner* — James H Alstrum Acevedo
*Assistant Examiner* — Thea D'Ambrosio
(74) *Attorney, Agent, or Firm* — Fish & Richardson P.C.

(57) ABSTRACT

Methods for treating fatty liver disease, e.g., hepatic steatosis, using peptide fragments of the C-terminal end of glucagon-like peptide-1 (GLP-1), e.g., GLP-1(28-36).

12 Claims, 8 Drawing Sheets

(56) References Cited

FOREIGN PATENT DOCUMENTS

| | | |
|---|---|---|
| EP | 1196444 B1 | 6/2003 |
| EP | 1329458 A2 | 7/2003 |
| EP | 0708179 | 12/2004 |
| WO | 91/11457 | 8/1991 |
| WO | WO 96/06628 | 3/1996 |
| WO | WO 98/08871 | 3/1998 |
| WO | WO 98/39022 | 9/1998 |
| WO | WO 99/38501 | 8/1999 |
| WO | WO 99/43705 | 9/1999 |
| WO | WO 99/43706 | 9/1999 |
| WO | WO 99/43708 | 9/1999 |
| WO | WO 99/53064 | 10/1999 |
| WO | WO 00/77039 | 12/2000 |
| WO | WO 01/37850 | 5/2001 |
| WO | WO 01/68603 | 9/2001 |
| WO | WO 01/98331 | 12/2001 |
| WO | WO 02/47716 | 6/2002 |
| WO | WO 02/062764 | 8/2002 |
| WO | WO 02/083128 | 10/2002 |
| WO | WO 02/085406 | 10/2002 |
| WO | WO 03/018516 | 3/2003 |
| WO | WO 03/028626 | 4/2003 |
| WO | WO 03/038123 | 5/2003 |
| WO | WO 03/045977 | 6/2003 |
| WO | WO 03/061362 | 7/2003 |
| WO | WO 03/072195 | 9/2003 |
| WO | WO 03/099991 | 12/2003 |
| WO | WO 03/103572 | 12/2003 |
| WO | 2005/060986 | 7/2005 |
| WO | WO 2007/051987 | 5/2007 |
| WO | WO 2007051987 A1 * 5/2007 ........... C07K 14/605 |
| WO | WO 2007/065156 | 6/2007 |
| WO | WO2009051259 A1 | 4/2009 |
| WO | 2010/054326 | 5/2010 |
| WO | WO 2010054326 A2 * 5/2010 ............... C07K 7/04 |
| WO | WO 2010/093802 | 8/2010 |
| WO | WO 2010093802 A2 * 8/2010 ............. C12N 5/071 |

OTHER PUBLICATIONS

Mu et al., "Chronic Inhibition of Dipeptidyl Peptidase-4 With a Sitagliptin Analog Preserves Pancreatic B-Cell Mass and Function in a Rodent Model of Type 2 Diabetes," Diabetes 55:1695-1704 (2006).*
U.S. Appl. No. 14/539,578, filed Nov. 2014, Habener et al.*
International Search Report in International Application No. PCT/US2011/058907, mailed May 25, 2012, 3 pages.
International Preliminary Report on Patentability in International Application No. PCT/US2011/058907, mailed May 16, 2013, 7 pages.
Abu-Hamdah et al., "Clinical review: The extrapancreatic effects of glucagon-like peptide-1 and related peptides," J. Clin. Endocrinol. Metab., 94:1843-52 (2009).
Ban et al., "Cardioprotective and vasodilatory actions of glucagon-like peptide 1 receptor are mediated through both glucagon-like peptide 1 receptor-dependent and -independent pathways," Circulation, 117:2340-50 (2008).
Ban et al., "Glucagon-like peptide (GLP)-1(9-36)amide-mediated cytoprotection is blocked by exendin (9-39) yet does not require the known GLP-1 receptor," Endocrinology, 151:1520-31 (2010).
Brun et al., "Intracellular targeting of truncated secretory peptides in the mammalian heart and brain," FASEB J., 20:732-734 (2006).
Deacon, "Circulation and degradation of GIP and GLP-1," Horm. Metab. Res., 36:761-5 (2004).
Elahi et al., "Glucagon-like peptide-1(9-36)amide, cleavage product of glucagon-like peptide-1 (7-36) is a glucoregulatory peptide," Obesity, 16:1501-9 (2008).
Farooqui et al., "Metabolic syndrome as a risk factor for neurological disorders," Cell. Mol. Life. Sci., 69:741-762 (2012) Epub ahead of print (2011).
Flock et al., "Incretin receptors for glucagon-like peptide 1 and glucose-dependent insulinotropic polypeptide are essential for the sustained metabolic actions of vildagliptin in mice," Diabetes, 56:3006-13 (2007).

Grattagliano et al., "Oxidative stress-induced risk factors associated with the metabolic syndrome: a unifying hypothesis," J. Nutr. Biochem., 19:491-504 (2008).
Green et al., "GLP-1 and related peptides cause concentration-dependent relaxation of rat aorta through a pathway involving KATP and cAMP," Arch. Biochem., Biophys., 478:136-42 (2008).
Haas et al., "Dissecting the Role of Insulin Resistance in the Metabolic Syndrome," Curr. Opin. Lipidol., 20:206-210 (2009).
Hansen et al., "Glucagon-like peptide-1-(7-36)amide is transformed to glucagon-like peptide-1-(9-36)amide by dipeptidyl peptidase IV in the capillaries supplying the L cells of the porcine intestine," Endocrinology, 140:5356-63 (1999).
Hirst, "Towards the molecular mechanism of respiratory complex I," J. Biochem., 425:327-339 (2009).
Hupe-Sodmann et al., "Characterisation of the processing by human neutral endopeptidase 24.11 of GLP-1(7-36) amide and comparison of the substrate specificity of the enzyme for other glucagon-like peptides," Regul. Pept., 58:149-156 (1995).
Kieffer and Habener, "The glucagon-like peptides," Endocr. Rev., 20:876-913 (1999).
Larter et al., "MCD-induced steatohepatitis is associated with hepatic adiponectin resistance and adipogenic transformation of hepatocytes," J Hepatol., 49:407-416 (2008).
Liu et al., "Prolonged treatment of primary hepatocytes with oleate induces insulin resistance through p38 mitogen-activated protein kinase," J. Biol. Chem., 282:14205-14212 (2007).
Lovshin and Drucker, "Incretin-based therapies for type 2 diabetes mellitus," Nat. Rev. Endocrinol., 5:262-9 (2009).
Luchsinger, "Diabetes, related conditions, and dementia," J Neurol Sci., 299:35-38 (2010).
Meier et al., "The glucogon-like peptide-1 metabolite GLP-1(9-36)amide reduces postprandial glycemia independently of gastric emptying and insulin secretion in humans," Am. J. Physiol. Endocrinol. Metab., 290:E1118-E1123 (2006).
Nikolaidis et al., "Active metabolite of GLP-1 mediates myocardial glucose uptake and improves left ventricular performance in conscious dogs with dilated cardiomyopathy," Am. J. Physiol. Heart Circ. Physiol., 289:H2401-2408 (2005).
Ott et al., "Mitochondria, oxidative stress and cell death," Apoptosis, 12:913-922 (2007).
Panza et al., "Metabolic syndrome and Cognitive Impairment: Current Epidemiology and Possible Underlying Mechanisms," J. Alzheimers Dis., 21:691-724 (2010).
Parekh et al., "Reversal of diet-induced obesity and diabetes in C57BL/6J mice," Metabolism, 47:1089-1096 (1998).
Plamboeck et al., "Neutral endopeptidase 24.11 and dipeptidyl peptidase IV are both mediators of the degradation of glucagon-like peptide 1 in the anaesthetized pig.," Diabetologia, 48:1882-90 (2005).
Randle, "Regulatory interactions between lipids and carbohydrates: the glucose fatty acid cycle after 35 years," Diabetes Metab Rev., 14:263-83 (1998).
She et al., "Adipogenic Transcriptional Regulation of Hepatic Stellate Cells," J, Biol, Chem,, 280:4959-4967 (2005).
Simonsen et al., "Inhibition of neutral endopeptidase 24.11 does not potentiate the improvement in glycemic control obtained with dipeptidyl peptidase-4 inhibition in diabetic Goto-Kakizaki rats," Horm. Metab. Res., 41:851-3 (2009).
Sonne et al., "Protective effects of GLP-1 analogues exendin-4 and GLP-1(9-36) amide against ischemia-reperfusion injury in rat heart," Regul. Pept., 146:243-9 (2008).
Stein et al., "Insulin sensitizers in nonalcoholic fatty liver disease and steatohepatitis," Current Status Advanced Ther., 26:893-907 (2009).
Tomas and Habener, "Insulin-like actions of glucagon-like peptide-1: A dual receptor hypothesis," Trends Endocrinol. Metab., 21:59-67 (2010).
Tomas et al., "GLP-1(9-36)amide metabolite suppression of glucose production in isolated mouse hepatocytes," Horm. Metab. Res., 42:657-662 (2010).
Tsukamoto et al., "Fat paradox of steatohepatitis," J Gastroenterol Hepatol., 23 Suppl 1:S104-107 (2008).
Unger et al., "Lipid homeostasis, lipotoxicity and the metabolic syndrome," Biochimica et Biophysica Acta., 1801:209-214 (2010).

(56) References Cited

OTHER PUBLICATIONS

Zhang et al., "Continuous stimulation of human glucagon-like peptide-1 (7-36) amide in a mouse model (NOD) delays onset of autoimmune type 1 diabetes," Diabetologia, 50:1900-1909 (2007).
Zhao et al., "Cell-permeable Peptide Antioxidants Targeted to Inner Mitochondrial Membrane inhibit Mitochondrial Swelling, Oxidative Cell Death, and Reperfusion Injury," J. Biol. Chem., 279:34682-90 (2004).
Authier et al., "Endosomal Proteolysis of Glucagon at Neutral pH Generates the Bioactive Degradation Product Miniglucagon-(19-29)," Endocrinology, 144(12):5353-5364, Dec. 2003.
Bebernitz et al., "The Impact of Fatty Acid Oxidation on Energy Utilization: Targets and Therapy," Current Pharmaceutical Design, 8:1199-1227, Jun. 2002.
Communication issued in EP 09825560.7 on Apr. 15, 2014, 8 pages.
Dalle et al., "Miniglucagon (Glucagon 19-29) A Novel Regulator of the Pancreatic Islet Physiology," Diabetes, 51:406-412, Feb. 2002.
Dayhoff et al., "Establishing homologies in protein sequences," Methods Enzymol., 91:524-545, Jan. 1983.
De Meester et al., "CD26, let it cut or cut it down," Immunol. Today, 20:367-375, Aug. 1999.
Ding et al., "Exendin-4, a Glucagon-Like Protein-1 (GLP-1) Receptor Agonist, Reverses Hepatic Steatosis in ob/ob Mice," Hepatology, 43:173-181, Jan. 2006.
Dobrzyn et al., "Stearoyl-CoA desaturase 1 deficiency increases fatty acid oxidation by activating AMP-activated protein kinase in liver," Proc. Natl. Acad. Sci. USA, 101(17):6409-6414, Apr. 2004.
Drucker, "The biology of incretin hormones," Cell. Metab., 3:153-165, Mar. 2006.
Egan et al., "Glucagon-Like Peptide-1 Augments Insulin-Mediated Glucose Uptake in the Obese State," The Journal of Clinical Endocrinology & Metabolism, 87(8)3768-3773, Aug. 2002.
Elahi et al., "The Insulinomimetic Actions of GLP-1(9-36) Amide, Cleavage Product of GLP-1(7-36) Amide," Diabetes, 55(Suppl 1):A85 (Abstract 363-OR), 2006.
Ferrand et al., "Involvement of JAK2 upstream of the PI 3-kinase in cell-cell adhesion regulation by gastrin," Exp. Cell. Res., 301:128-138, Dec. 2004.
Hashimoto et al., "A new inhibitor of mitochondrial fatty acid oxidation," J. Biochem., 119(6):1196-1201, Jun. 1996.
Ibdah et al., "Lack of mitochondrial trifunctional protein in mice causes neonatal hypoglycemia and sudden death," J. Clin. Invest., 107:1403-1409, 2001.
Ibdah et al., "Mice Heterozygous for a Defect in Mitochondrial Trifunctional Protein Develop Hepatic Steatosis and Insulin Resistance," Gastroenterology, 128:1381-1390, May 2005.
International Preliminary Report on Patentability in International Application No. PCT/US2012/045537, mailed Jan. 16, 2014, 8 pages.
International Search Report and Written Opinion in International Application No. PCT/US2012/045537, mailed Jan. 29, 2013, 16 pages.
International Search Report issued in PCT/US2009/063746 on Jun. 29, 2010, 15 pages.
Knudsen et al., "Glucagon-like peptide-1-(9-36) amide is a major metabolite of glucagon-like peptide-1-(7-36) amide after in vivo administration of dogs, and it acts as an antagonist on the pancreatic receptor," European Journal of Pharmacology, 318:429-435, Dec. 1996.

Knudsen et al., "Potent derivatives of glucagon-like peptide-1 with pharmacokinetic properties suitable for once daily administration," J. Med. Chem., 43:1664-1669, May 2000.
Koonen et al., "Increased hepatic CD36 expression contributes to dyslipidemia associated with diet-induced obesity," Diabetes, 56:2863-2871, Dec. 2007.
Lambeir et al., "Dipeptidyl-peptidase IV from bench to bedside: an update on structural properties, functions, and clinical aspects of the enzyme DPP IV," Crit. Rev. Clin. Lab. Sci., 40:209-294, Jun. 2003.
Li et al., "GLP-1 C-terminal structures affect its blood glucose lowering function," Journal of Peptide Science, 14:777-785, Jul. 2008.
Meneilly et al., "Effects of 3 Months of Continuous Subcutaneous Administration of Glucagon-Like Peptide 1 in Elderly Patients with Type 2 Diabetes," Diabetes Care, 26(10):2835-2841, Oct. 2003.
Murphy et al., "Gastrin and gastrin receptor antagonists bind to both N- and C-terminal halves of the 78 kDa gastrin-binding protein," Int. J. Biochem. Cell. Biol., 28:1233-1240, Nov. 1996.
Plamboeck et al., "Neutral endopeptidase 24.11 and dipeptidyl peptidase IV are both involved in regulating the metabolic stability of glucagon-like peptide-1 in vivo," Adv Exp Med Biol., 524:303-12, 2003.
Rodrigue-Way et al., "A growth hormone-releasing peptide promotes mitochondrial biogenesis and a fat burning-like phenotype through scavenger receptor CD36 in white adipocytes," Endocrinology, 148(3):1009-1018, Mar. 2007.
Roques et al., "Neutral endopeptidase 24.11: structure, inhibition, and experimental and clinical pharmacology," Pharmacol. Rev., 45:87-146, Mar. 1993.
Ryan et al., "Insulinotropic Hormone Glucagon-Like Peptide-1-(7-37) Appears Not to Augment Insulin-Mediated Glucose Uptake in Young Men during Euglycemia," Journal of Clinical Endocrinology and Metabolism, 83(7):2399-2404, 1998.
Sato et al., "Therapeutic peptides: technological advances driving peptides into development," Current Opinion in Biotechnology, 17(6):638-642, Dec. 2006.
Standeven et al., "Neprilysin, obesity and the metabolic syndrome," Int J Obes (Lond), Nov. 1-10, 2010.
Supplementary European Search Report issued in EP09825560 on Feb. 7, 2012.
Todd et al., "Glucagon-like peptide-1 (GLP-1): a trial of treatment in non-insulin-dependent diabetes mellitus," European Journal of Clinical Investigation, 27:533-536, Jun. 1997.
Tomas et al., "GLP-1-derived nonapeptide GLP-1(28-36) amide inhibits weight gain and attenuates diabetes and hepatic steatosis in diet-induced obese mice," Regulatory Peptides, 169(1-3):43-48, May 2011.
Tomas et al., "GLP-1-derived nonapeptide GLP-1(28-36) amide targets to mitochondria and suppresses glucose production and oxidative stress in isolated mouse hepatocytes," Regulatory Peptides, 167(2-3):177-184, Jan. 2011.
Tomas et al., "Glucagon-like peptide-1(9-36)amide metabolite inhibits weight gain and attenuates diabetes and hepatic steatosis in diet-induced obese mice," Diabetes Obes Metab., 13:26-33, Jan. 2011.
Wanders et al., "Disorders of mitochondrial fatty acyl-CoA β-oxidation," J. Inher. Metab. Dis., 22:442-487, Jun. 1999.
Zander et al., "Effect of 6-week course of glucagon-like peptide 1 on glycaemic control, insulin sensitivity, and betta-cell function in type 2 diabetes: a parallel-group study," The Lancet, 359:824-830, Mar. 2002.

* cited by examiner

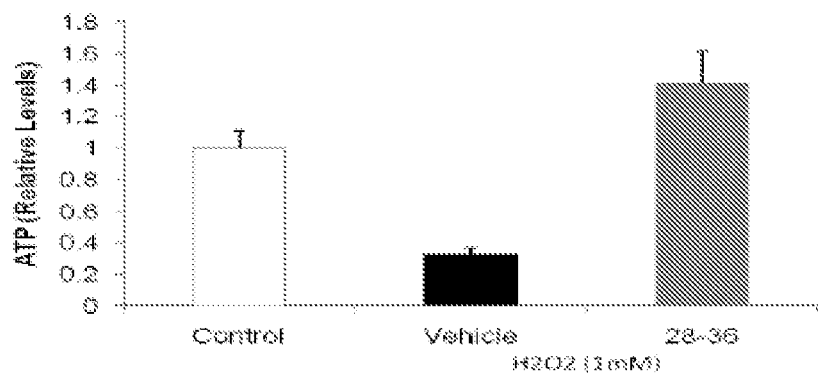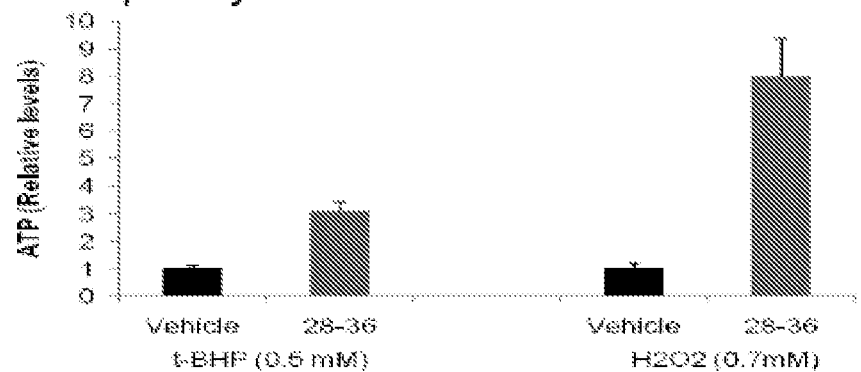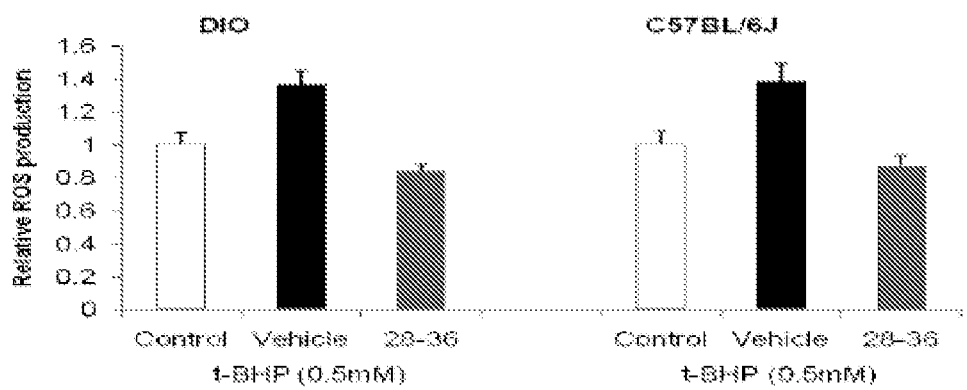
FIGs. 3A-C p< 0.0006 30 mM vs. 5 mM
(*) p< 0.02
(**) p< 0.0021

SEQUENCE LISTING

<160> NUMBER OF SEQ ID NOS: 15

<210> SEQ ID NO 1
<211> LENGTH: 9
<212> TYPE: PRT
<213> ORGANISM: Artificial Sequence
<220> FEATURE:
<223> OTHER INFORMATION: synthetically generated peptides

<400> SEQUENCE: 1

Phe Ile Ala Trp Leu Val Lys Gly Arg
 1               5

<210> SEQ ID NO 2
<211> LENGTH: 30
<212> TYPE: PRT
<213> ORGANISM: Artificial Sequence
<220> FEATURE:
<223> OTHER INFORMATION: synthetically generated peptides

<400> SEQUENCE: 2

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
             20                  25                  30

<210> SEQ ID NO 3
<211> LENGTH: 5
<212> TYPE: PRT
<213> ORGANISM: Artificial Sequence
<220> FEATURE:
<223> OTHER INFORMATION: synthetically generated peptides

<400> SEQUENCE: 3

Leu Val Lys Gly Arg
 1               5

<210> SEQ ID NO 4
<211> LENGTH: 10
<212> TYPE: PRT
<213> ORGANISM: Artificial Sequence
<220> FEATURE:
<223> OTHER INFORMATION: synthetically generated peptides

<400> SEQUENCE: 4

Phe Ile Ala Trp Leu Val Lys Gly Arg Gly
 1               5                  10

<210> SEQ ID NO 5
<211> LENGTH: 11
<212> TYPE: PRT
<213> ORGANISM: Artificial Sequence
<220> FEATURE:
<223> OTHER INFORMATION: synthetically generated peptides

<400> SEQUENCE: 5

Phe Ile Ala Trp Leu Val Lys Gly Arg Gly Arg
 1               5                  10

<210> SEQ ID NO 6
<211> LENGTH: 9
<212> TYPE: PRT
<213> ORGANISM: Artificial Sequence
<220> FEATURE:
<223> OTHER INFORMATION: synthetically generated peptides

<400> SEQUENCE: 6

```
Phe Ile Ala Trp Arg Val Lys Gly Arg
 1               5

<210> SEQ ID NO 7
<211> LENGTH: 9
<212> TYPE: PRT
<213> ORGANISM: Artificial Sequence
<220> FEATURE:
<223> OTHER INFORMATION: synthetically generated peptides

<400> SEQUENCE: 7

Tyr Ile Ala Trp Leu Val Lys Gly Arg
 1               5

<210> SEQ ID NO 8
<211> LENGTH: 11
<212> TYPE: PRT
<213> ORGANISM: Artificial Sequence
<220> FEATURE:
<223> OTHER INFORMATION: synthetically generated peptides
<220> FEATURE:
<221> NAME/KEY: VARIANT
<222> LOCATION: 1
<223> OTHER INFORMATION: Xaa = Ala-Lys-Glu or absent
<220> FEATURE:
<221> NAME/KEY: VARIANT
<222> LOCATION: 2
<223> OTHER INFORMATION: Xaa = Phe or Tyr
<220> FEATURE:
<221> NAME/KEY: VARIANT
<222> LOCATION: 8
<223> OTHER INFORMATION: Xaa = Lys/Arg
<220> FEATURE:
<221> NAME/KEY: VARIANT
<222> LOCATION: 11
<223> OTHER INFORMATION: Xaa = Gly, Gly-Arg, Gly-Arg-Gly, or absent

<400> SEQUENCE: 8

Xaa Xaa Ile Ala Trp Leu Val Xaa Gly Arg Xaa
 1               5                   10

<210> SEQ ID NO 9
<211> LENGTH: 10
<212> TYPE: PRT
<213> ORGANISM: Artificial Sequence
<220> FEATURE:
<223> OTHER INFORMATION: synthetically generated peptides
<220> FEATURE:
<221> NAME/KEY: VARIANT
<222> LOCATION: 1
<223> OTHER INFORMATION: Xaa = Phe or Tyr
<220> FEATURE:
<221> NAME/KEY: VARIANT
<222> LOCATION: 7
<223> OTHER INFORMATION: Xaa = Lys or Arg
<220> FEATURE:
<221> NAME/KEY: VARIANT
<222> LOCATION: 10
<223> OTHER INFORMATION: Xaa = Gly, Gly-Arg, Gly-Arg-Gly

<400> SEQUENCE: 9

Xaa Ile Ala Trp Leu Val Xaa Gly Arg Xaa
 1               5                   10

<210> SEQ ID NO 10
<211> LENGTH: 9
<212> TYPE: PRT
<213> ORGANISM: Artificial Sequence
<220> FEATURE:
<223> OTHER INFORMATION: synthetically generated peptides
```

```
<400> SEQUENCE: 10

Arg Gly Lys Val Leu Trp Ala Ile Phe
1               5

<210> SEQ ID NO 11
<211> LENGTH: 10
<212> TYPE: PRT
<213> ORGANISM: Artificial Sequence
<220> FEATURE:
<223> OTHER INFORMATION: synthetically generated peptides

<400> SEQUENCE: 11

Gly Arg Gly Lys Val Leu Trp Ala Ile Phe
1               5                   10

<210> SEQ ID NO 12
<211> LENGTH: 11
<212> TYPE: PRT
<213> ORGANISM: Artificial Sequence
<220> FEATURE:
<223> OTHER INFORMATION: synthetically generated peptides

<400> SEQUENCE: 12

Arg Gly Arg Gly Lys Val Leu Trp Ala Ile Phe
1               5                   10

<210> SEQ ID NO 13
<211> LENGTH: 10
<212> TYPE: PRT
<213> ORGANISM: Artificial Sequence
<220> FEATURE:
<223> OTHER INFORMATION: synthetically generated peptides

<400> SEQUENCE: 13

Leu Arg Arg Arg Leu Ser Asp Ala Asn Phe
1               5                   10

<210> SEQ ID NO 14
<211> LENGTH: 10
<212> TYPE: PRT
<213> ORGANISM: Artificial Sequence
<220> FEATURE:
<223> OTHER INFORMATION: synthetically generated peptides

<400> SEQUENCE: 14

Gly Arg Arg Glu Ser Leu Thr Ser Phe Gly
1               5                   10

<210> SEQ ID NO 15
<211> LENGTH: 10
<212> TYPE: PRT
<213> ORGANISM: Artificial Sequence
<220> FEATURE:
<223> OTHER INFORMATION: synthetically generated peptides

<400> SEQUENCE: 15

Asp Arg Val Tyr Ile His Pro Phe His Leu
1               5                   10
```

US 9,040,481 B2

METHODS FOR TREATING STEATOTIC DISEASE

CLAIM OF PRIORITY

This application is a U.S. National Phase application under 35 U.S.C. §371 of International Patent Application No. PCT/US2011/058907, filed Nov. 2, 2011 and claims the benefit of U.S. Provisional Patent Application Ser. Nos. 61/409,288, filed on Nov. 2, 2010, and 61/416,128, filed Nov. 22, 2010. The entire contents of the foregoing are hereby incorporated by reference.

TECHNICAL FIELD

This invention relates to methods for treating fatty liver disease, e.g., hepatic steatosis, and dystipidemia, e.g., hyperlipidemia, using peptide fragments of the C-terminal end of glucagon-like peptide-1 (GLP-1), GLP-1(28-36).

BACKGROUND

Steatotic diseases start out as ectopic lipid deposition in extra-adipose epithelial tissues. The lipid deposition raises oxidative stress in the affected cells and recruits an inflammatory response. Fatty liver disease begins with ectopic lipid deposition in hepatocytes, steatosis (e.g., non-alcoholic fatty liver disease (NAFLD)), progressing to inflammation (non-alcoholic steatohepatitis (NASH)), then to fibrosis and scarring (cirrhosis) ultimately to hepatocellular carcinoma or liver failure.

SUMMARY

The invention is based, at least in part, on the discovery that peptide fragments of the C-terminal end of glucagon-like peptide-1 (GLP-1), and analogs thereof, modulate oxidative phosphorylation, reduces oxidative stress (lowers levels of reactive oxygen species) inhibits gluconeogenesis, suppresses oxidative stress, raises MT levels, inhibits apoptosis, and enhances cell survival. When infused into high fat diet-induced obese mice GLP-1(28-36)amide curtails weight gain, increases energy expenditure, improves insulin sensitivity (attenuates hyperglycemia and hyperinsulinemia), and decreases or prevents the development of hepatic steatosis. Therefore, based on these demonstrated properties of GLP-1 (28-36)amide in cell cultures, and in diet-induced obese mice, GLP-1(28-36)amide is an effective treatment for steatotic disease, e.g., fatty liver disease, e.g., hepatic steatosis. Furthermore, as hepatic steatosis is associated with hyperlipidemia, the peptides are useful in treating subjects with elevated lipid levels as well.

Thus, in one aspect, the invention features methods for treating or preventing a fatty liver disease (FLD) in a subject, e.g., a mammal. The methods include administering to the mammal a therapeutically effective amount of a peptide consisting essentially of (Phe/Tyr)-Ile-Ala-Trp-Leu-Val-(Lys/Arg)-Gly-Arg-Xaa (SEQ ID NO:9), wherein Xaa can be Gly, Gly-Arg, Gly-Arg-Gly, or absent.

In another aspect, the invention is directed to a method of treating a dyslipidemia, e.g., reducing levels of LDL, total cholesterol, or serum triglycerides in a subject (e.g., a mammal), the method comprising administering to the subject a therapeutically effective amount of a peptide consisting essentially of (Phe/Tyr)-Ile-Ala-Trp-Leu-Val-(Lys/Arg)-Gly-Arg-Xaa (SEQ ID NO:9), wherein Xaa can be Gly, Gly-Arg, Gly-Arg-Gly, or absent.

In an additional aspect, the invention provides compositions comprising a peptide consisting essentially of (Phe/Tyr)-Ile-Ala-Trp-Leu-Val-(Lys/Arg)-Gly-Arg-Xaa (SEQ ID NO:9), wherein Xaa can be Gly, Gly-Arg, Gly-Arg-Gly, or absent, for use in treating or preventing a dyslipidemia or a fatty liver disease (FLD) in a mammal. In some embodiments, the peptide is formulated for oral administration.

In some embodiments, the peptide is GLP-1(28-36) (SEQ ID NO:1).

In some embodiments, the peptide is amidated, acetylated, or both.

In some embodiments, one or more amino acids are modified by attachment of a fatty acid, e.g., a fatty acid is selected from the group consisting of palmitate and oleate.

In some embodiments, the peptide is fused to a cell-penetrating peptide, e.g., the cell-penetrating peptide is fused on the C-terminus of the peptide. In some embodiments, the cell-penetrating peptide is selected from the group consisting of FITV-derived TAT peptide, penetratins, transportans, SS peptides, and hCT derived cell-penetrating peptides.

In some embodiments, the mammal has Nonalcoholic Steatohepatitis (NASH) or is at risk of developing NASH, or has Nonalcoholic Fatty Liver Disease (NAFLD) or is at risk of developing NAFLD.

In some embodiments, the subject has elevated levels of total cholesterol, or triglycerides.

In some embodiments, the methods further include selecting the mammal on the basis that they have or are at risk of developing a HD, e.g., NASH or NAFLD.

In some embodiments, the methods further include evaluating fatty liver disease in the subject, before, during, or after administration of the inhibitor.

In some embodiments, the administration is oral administration.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 3A is a bar graph showing the results of experiments in which a H4IIe hepatocyte cell line was treated with vehicle control or GLP-1(28-36)amide (100 nM) and exposed to $H_2O_2$ (1.0 mM) for 24 hours.

FIG. 3B is a bar graph showing cellular ATP levels in hepatocytes isolated from diet-induced obese (DIO) mice pre-treated overnight with either vehicle control (Vehicle) GLP-1(28-36)amide (28-36). tert-butyryl hydroperoxide (tBHP) (0.5 mM) or $H_2O_2$ (0.7 mM) was added for one hour or overnight respectively prior to harvesting and extracting the cells for ATP assay. Control cells, left open bar, were not treated with $H_2O_2$.

FIG. 3C is a bar graph showing inhibition of production of reactive oxygen species (ROS) by GLP-1(28-36)amide in hepatocytes isolated from DIO mice (left panel) and normal C57bl/6J mice (right panel), Hepatocytes were pre-treated overnight with vehicle alone or with GLP-1(28-36)amide (100 nM) and were then exposed to tBHP (0.5 mM) for one hour. Cells were extracted and assayed for ROS content (see Methods), Control cells, left open bar, are cells not treated with tBHP.

DETAILED DESCRIPTION

Figure 1:
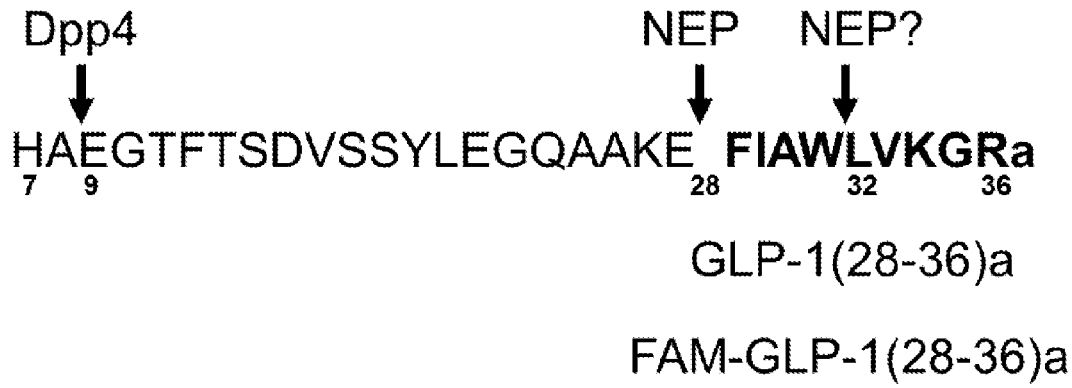
FIG. 1 shows the amino acid sequence of GLP-1(7-36) amide (SEQ ID NO:2) showing proteolytic cleavage sites by the enzymes diaminopeptidyl peptidase-4 (Dpp4) and neutral endopeptidase (NEP). GLP-1(28-36)amide consists of the carboxlyl-terminal nine amino acids. It remains possible that an endopeptidase also cleaves between tryptophan (W) and leucine (L), positions 31 and 32, to produce the pentapeptide, LVKGRamide (SEQ ID NO:3), thus the methods described herein may also or alternatively include the administration of this pentapeptide. The nonapepteide was labeled at the amino-terminus by the addition of 5-carboxy-fluoroscein (FAM), a fluorescence adduct, for addition to hepatocytes along with Mitotracker.

Adipose is believed to be a depot for the storage of lipids where they belong, do no harm, and can serve as a reservoir for energy when needed. When adipose stores become filled, the lipids spill over into the circulation, resulting in elevated plasma lipids (dyslipidemia). Then the lipids are deposited in parenchymal tissues where they should not be, like the liver. This is ectopic fat deposition (extra adipocytic deposition, called steatosis.

Liver, heart, skeletal muscle, vasculature, and other organs suffer from ectopic fat deposition in some obese individuals. Obesity, dyslipidemia, and metabolic syndrome are risk factors for neurodegenerative disorders and dementia (Farooqui et al, "Metabolic syndrome as a risk factor for neurological disorders" Cell Mol Life Sci, 2011. Epub ahead of print; Luchsinger, J Neurol Sci. (2010) 299:35-38, Panza et al. Alzheimers Dis. (2010) 21:691-724). Although firm causation data on ectopic fat deposition in brain (e.g. in neurons and glia) has not yet been developed, there is strong epidemiological evidence of an association of dyslipidemia, obesity, and type 2 diabetes with the development of neurodegenerative diseases, e.g., dementia and Huntington's disease. Ectopic fat recruits an inflammatory response, then progresses to fibrosis. Steatosis is a component of the metabolic syndrome, Fatty liver cells may actually transdifferentiate into an adipocyte phenotype (see, e.g., Tsukamoto et al., J Gastroenterol Hepatol. (2008) March; 23 Suppl 1:S104-107; She et al. J Biol. Chem. (2005) 280:4959-4967 2005; Larter et al., J. Hepatol. (2008) 49:407-416), which may be a result of the body's attempt to store excess lipids where they belong. Experimental injuries of liver have been shown to transdifferentiate hepatocytes into an adipocyte phenotype (Larter et al., J. Hepatol. (2008) 49:407-416) and liver stellate cells are shown to differentiate into adipocytes (Tsukamoto et al., Gastroenterol Hepatol. (2008) March; 23 Suppl 1:S104-107). The adipocyte overflow notion has been proposed as the basis for metabolic syndrome. See, e.g., Unger et al., Biochimica et Biophysica Acta (2010) 1801:209-214.

As described herein, GLP-1(28-36) rapidly (e.g., within about 15 minutes) selectively enters stressed hepatocytes, and targets to the mitochondria, where it modulates oxidative phosphorylation, reduces oxidative stress (lowers levels of reactive oxygen species) inhibits gluconeogenesis, suppresses oxidative stress, raises ATP levels, inhibits apoptosis, and enhances cell survival. When infused into high fat diet-induced mice, GLP-1(28-36) curtails weight gain, increases energy expenditure, improves insulin sensitivity (attenuates hyperglycemia and hyperinsulinemia), and decreases or prevents the development of hepatic steatosis. Therefore, based on these demonstrated properties of these GLP-1 peptides in cell cultures, and in diet-induce obese mice, we propose that these GLP-1 peptides, and peptidomimetics or analogues thereof, will be an effective treatment for dyslipidemia and steatotic disease, e.g., fatty liver disease, e.g., hepatic steatosis.

GLP-1 C-Terminal Peptides, Fusion Peptides. Peptidomimetics, and Modifications

The GLP-1 C-terminal peptides described herein include the sequence FIAWLVKGR (SEQ ID NO:1), or a variant thereof. Variants include peptides in which the sequence is C-terminally extended, e.g., FIAWLVKGRG (SEQ ID NO:4), FIAWRVKGRGR (SEQ ID NO:5), or FIAWLVKGRGRamide (SEQ ID NO:5), or in which one or more amino acids are conservatively substituted, for example FIAWRVKGRamide (SEQ ID NO:6), in which Lysine 32 (the numbering refers to the full-length GLP-1) is changed to Arginine, or in which Phenylalanine28 is changed to Tyrosine (YIAWLVKGRamide (SEQ ID NO:7)). In some embodiments the peptides also include the sequence AKE on the N-terminus.

Thus in some embodiments, the peptides described herein can have the sequence Xaa$_1$-(Phe/Tyr)-Ile-Ala-Trp-Leu-Val-(Lys/Arg)-Gly-Arg-Xaa$_2$ (SEQ ID NO:8), wherein Xaa$_1$ can be Ala-Lys-Glu, or absent, and Xaa$_2$ can be Gly, Gly-Arg, Gly-Arg-Gly, or absent.

In some embodiments, the peptides described herein can have the sequence (Phe/Tyr)-Ile-Ala-Trp-Leu-Val-(Lys/Arg)-Gly-Arg-Xaa (SEQ ID NO:9), wherein Xaa can be Gly, Gly-Arg, Gly-Arg-Gly, or absent.

Methods for making these peptides are known in the art, e.g., using chemical synthesis or expression in a host cell.

Fusion Peptides

In some embodiments, the peptides also include a cell-penetrating moiety that facilitates delivery of the peptides to the intracellular space, e.g., HIV-derived TAT peptide, penetratins, transportans, SS peptides (alternating aromatic residues and basic amino acids (aromatic-cationic peptides)), SA, SM, or SNL peptides, or hCT derived cell-penetrating peptides, see, e.g., Caron et al., (2001) Mol Ther. 3(3):310-8; Langel, *Cell-Penetrating Peptides Processes and Applications* (CRC Press, Boca Raton Fla. 2002); El-Andaloussi et al., (2005) Curr Pharm Des. 11(28):3597-611; Lindgren et al., Trends Pharmacol Sci. 21(3):99-103 (2000); Zhao et al., J Biol Chem 279:34682-34690 (2004); Szeto, AAPS Journal 2006; 8 (2) Article 32; Deshayes et al., (2005) Cell Mol Life Sci. 62(16):1839-49; Horn et al., J. Med. Chem., 46:1799 (2003); Bonny et al., Diabetes, 50:77-82 (2001), and U.S. Pat. Nos. 6,841,535 and 7,576,058 and references cited therein. In some embodiments the cell-penetrating moiety is linked to the peptide, e.g., as a single fusion protein; thus, the invention includes fusion proteins comprising a GLP-1 C-terminal peptide as described herein and a cell-penetrating peptide, e.g., TAT, penetratins, transportans, or hCT derived cell-penetrating peptides. In some embodiments, the cell-penetrating peptide is attached to the N-terminus of the GLP-1 C-terminal peptide; in some embodiments, the cell-penetrating peptide is attached to the C-terminus of the GLP-1 C-terminal peptide. In some embodiments, the fusion protein further comprises a cleavable moiety as known in the art between the cell-penetrating peptide and the GLP-1 C-terminal peptide that cleaves of the cell-penetrating peptide, leaving the GLP-1 C-terminal peptide intact.

Peptidomimetics

In some embodiments, the peptides disclosed herein can be modified according to the methods known in the art for producing peptidomimetics, See, e.g., Kazmierski, W. M., ed., Peptidomimetics Protocols, Human Press (Totowa N.J. 1998); Goodman et al., eds., Houben-Weyl Methods of Organic Chemistry: Synthesis of Peptides and Peptidomimetics, Thiele Verlag (New York 2003); and Mayo et al., J. Biol. Chem., 278:45746 (2003). In some cases, these modified peptidomimetic versions of the peptides and fragments disclosed herein exhibit enhanced stability in vivo, relative to the non-peptidomimetic peptides.

Methods for creating a peptidomimetic include substituting one or more, e.g., of the amino acids in a peptide sequence with D-amino acid enantiomers. Such sequences are referred to herein as "retro" sequences. In another method, the N-terminal to C-terminal order of the amino acid residues is reversed, such that the order of amino acid residues from the N terminus to the C terminus of the original peptide becomes the order of amino acid residues from the C-terminus to the N-terminus in the modified peptidomimetic. Such sequences can be referred to as "inverso" sequences.

Peptidomimetics can be both the retro and inverso versions, i.e., the "retro-inverso" version of a peptide disclosed herein. The new peptidomimetics can be composed of D-amino acids arranged so that the order of amino acid residues from the N-terminus to the C-terminus in the peptidomimetic corresponds to the order of amino acid residues from the C-terminus to the N-terminus in the original peptide.

Other methods for making a peptidomimetics include replacing one or more amino acid residues in a peptide with a chemically distinct but recognized functional analog of the amino acid, an artificial amino acid analog. Artificial amino acid analogs include beta-amino acids, beta-substituted beta-amino acids ("beta3-amino acids"), phosphorous analogs of amino acids, such as b-amino phosphonic acids and b-amino phosphinic acids, and amino acids having non-peptide linkages. Artificial amino acids can be used to create peptidomimetics, such as peptoid oligomers (e.g., peptoid amide or ester analogues), beta-peptides, cyclic peptides, oligourea or oligocarbamate peptides; or heterocyclic ring molecules. Exemplary retro-inverso peptidontimetics include RGKVLWAIF (SEQ ID NO:10), GRGKVLWAIF (SEQ ID NO:11), or RGRGKVLWAIF (SEQ ID NO:12), wherein the sequences include all D-amino acids.

Modifications

The peptide sequences described herein can be modified, e.g., by modification of one or more amino acid residues of a peptide by chemical means, either with or without an enzyme, e.g., by alkylation, acetylation, acylation, methylation, ADP-ribosylation, ester formation, amide formation, e.g., at the carboxy terminus, or biotinylation, e.g., of the amino terminus. In some embodiments, the peptides are acetylated, e.g., on the free N6 epsilon amino group of Lys34 or on a guanidinium group nitrogen of Arg36 (the sequence VKGR is a good histone consensus motif for acetylation). In some embodiments, the peptides are amidated. Methods known in the art can be used to amidate or acetylate the peptides.

In some embodiments, the peptides are modified by the addition of a lipophilic substituent (e.g., a fatty acid) to an amino acid, e.g., to the Lysine. In some embodiments, the peptides include one or more of an N-terminal imidazole group, or a C-terminal amide group. In some embodiments, the epsilon-amino group of Lys34 is substituted with a lipophilic substituent, e.g., of about 4-40 carbon atoms, e.g., 8-25 carbon atoms. Examples include branched and unbranched C6-C20 acyl groups. Exemplary lipophilic substituents, and methods of attaching the same (including via an optional linker) are provided in U.S. Pat. No. 6,268,343 and Knudsen et al., J. Med. Chem. 43:1664-1669 (2000). In some embodiments, the lipophilic substituent is a fatty acid selected from the group consisting of straight-chain or branched fatty acids, e.g., oleic acid, caprylic acid, palmitic acid, and salts thereof.

In some embodiments, the peptide sequences are modified by substituting one or more amino acid residues of the parent peptide with another amino acid residue. In some embodiments, the total number of different amino acids between the sequence-modified peptide and the corresponding native form of the GLP-1 C-terminal peptide is up to five, e.g., up to four amino acid residues, up to three amino acid residues, up to two amino acid residues, or one amino acid residue.

In some embodiments, the total number of different amino acids does not exceed four. In some embodiments, the number of different amino acids is three, two, or one. In order to determine the number of different amino acids, one should compare the amino acid sequence of the sequence-modified GLP-1 peptide derivative with the corresponding native GLP-1 C-terminal fragment.

A number of suitable GLP-1 sequence analogues and modifications are described in the art, see, e.g., EP 0708179; WO 91/11457; U.S. Pat. No. 6,268,343). Peptides useful in the present methods are described in WO2010/054326, incorporated herein in its entirety.

Methods of Treatment

The methods described herein include methods for the treatment or prevention of hyperlipidemia and steatotic disease, i.e., diseases associated with abnormal retention of lipids (e.g., triglycerides) within a cell, e.g., fatty liver disease. Fatty liver disease is a condition in which triglyceride fats accumulate in liver cells. In some embodiments, the disorder is NASH or NAFLD, e.g., associated with obesity or the metabolic syndrome. In some embodiments, the disorder is fatty liver disease associated with exposure to one or more hepatoxins, e.g., alcohol, amiodarone, methotrexate, diltiazem, highly active antiretroviral therapy, glucocorticoids, tamoxifen, or environmental hepatoxins (e.g., phosphorus or mushroom poisoning). See, e.g., Reddy and Rao, Am. J. Physiol. Gastrointest. Liver Physiol. 290 (5): 6852-8 (2006); Angulo, N. Engl. J. Med. 346 (16): 1221-31 (2002); and Bayard et al., American family physician 73 (11): 1961-8 (2006). In some embodiments, the methods include identifying a subject who has a steatotic (e.g., fatty liver) disease, based on methods known in the art, optionally selecting the subject on the basis that they have a steatotic (e.g., fatty liver) disease, and administering a therapeutically effective amount of a GLP-1 C-terminal peptide or peptidomimetic as described herein, to a subject who is in need of, or who has been determined to be in need of, such treatment. In some embodiments, the methods include identifying a subject who has a dyslipidemia elevated total cholesterol, LDL, or triglycerides), based on methods known in the art, optionally selecting the subject on the basis that they have a dyslipidemia, and administering a therapeutically effective amount of a GLP-1 C-terminal peptide or peptidomimetic as described herein, to a subject who is in need of or who has been determined to be in need of such treatment.

As used in this context, to "treat" means to ameliorate at least one symptom of obesity or a disorder associated with steatotic disease. To "prevent" means to reduce risk of disease; a prevention need not reduce risk by 100%.

Administration of a therapeutically effective amount of a compound described herein for the treatment of fatty liver disease (FLD) will result in, e.g., a decrease or stabilization of fat levels in the liver; a decrease or stabilization of inflammation levels in the liver; or a reduction, delay or prevention of development of NASH, fibrosis, cirrhosis, or liver failure. In some embodiments, administration of a therapeutically effective amount of a compound described herein for the treatment of FLD will result in decreased or no increase in intra-cytoplasmic accumulation of triglyceride (neutral fats), and an improvement or no decline in liver function.

Administration of a therapeutically effective amount of a compound described herein for the treatment of dyslipidemia will result in, e.g., a decrease or stabilization of lipid levels in the blood, e.g., a return to or towards normal lipid levels, as shown in the tables below.

Fatty Liver Disease (FLD)

Nonalcoholic fatty liver disease (NAFLD) and its most severe form, nonalcoholic steatohepatitis (NASH), are associated with high fat diet, high triglyceride levels, obesity, the metabolic syndrome and type II diabetes, and pose an increased risk of cardiovascular disease. NAFLD is an accumulation of fat in the liver that is not a result of excessive consumption of alcohol. 15% to 25% of cases of NAFLD progress and are associated with inflammation and liver damage; this condition is referred to as NASH, NASH is associated with an increased risk of developing liver cirrhosis and subsequence complications, including hepatocellular carcinoma. FLD can be caused by excessive alcohol consumption (alcoholic hepatitis), drugs (such as valproic acid and corticosteroids (e.g., cortisone or prednisone)), excessive Vitamin A, and obesity. A diagnosis of NAFLD or NASH can be made by methods known in the art, e.g., by histological examination of liver biopsy samples.

In some embodiments, the methods include determining whether a subject has FLD, and selecting the subject if they do have FLD, then administering a dose of a GLP-1 C-terminal peptide or peptidomimetic as described herein. Determining whether a subject has FLD can include reviewing their medical history, or ordering or performing such tests as are necessary to establish a diagnosis.

Most individuals with FLD are asymptomatic; the condition is usually discovered incidentally as a result of abnormal liver function tests or hepatomegaly, e.g., noted in an unrelated medical condition. Elevated liver biochemistry is found in 50% of patients with simple steatosis (see, e.g.; Sleisenger, *Sleisenger and Fordtran's Gastrointestinal and Liver Disease*. Philadelphia: W.B. Saunders Company (2006)). In general, the diagnosis begins with the presence of elevations in liver tests that are included in routine blood test panels, such as alanine aminotransferase (ALT) or aspartate aminotransferase (AST). Even modest, subclinical increases in hepatic fat accumulation have been shown to be an early component in the progressive pathogenesis of metabolic syndrome (see, e.g., Almeda-Valdés et al., Ann. Hepatol. 8 Suppl 1:S18-24 (2009); Polyzos et al., Curr Mol. Med. 9(3):299-314 (2009); Byrne et al., Clin. Sci. (Lond). 116(7):539-64 (2009)).

Imaging studies are often obtained during evaluation process. Ultrasonography reveals a "bright" liver with increased echogenicity. Thus, medical imaging can aid in diagnosis of fatty liver; fatty livers have tower density than spleen on computed tomography (CT) and fat appears bright in T I-weighted magnetic resonance images (MRIs). Making a differential diagnosis of Nonalcoholic Steatohepatitis (NASH), as opposed to simple fatty liver, is done using a liver biopsy. For a liver biopsy, a needle is inserted through the skin to remove a small piece of the liver. NASH is diagnosed when examination of the tissue with a microscope shows fat along with inflammation and damage to liver cells. If the tissue shows fat without inflammation and damage, simple fatty liver or Nonalcoholic Fatty Liver Disease (NAFLD) is diagnosed. Thus, histological diagnosis by liver biopsy is sought when assessment of severity is indicated.

Non-Hepatic Steatosis

Although the liver is most often associated with steatosis, it can occur in any organ, including but not limited to skeletal muscle (see, e.g., Schmitz-Peiffer. Cell 2000 12(9-10):583-594) and vasculature (e.g., atherosclerosis), kidneys (renal steatosis, see, e.g., Bobulescu et al., Am J Physiol Renal Physiol. 2008 June; 294(6):F1315-22), heart (cardiac steatosis, see, e.g., McGavock et al., Circulation. 2007 Sep. 4; 116(10):1170-5; McGavock et al., Ann Intern. Med. 2006 Apr. 4; 144(7):517-24), thus, the present methods may also be used to treat those conditions. See, e.g., Federico et al., World Gastroenterol. 2010 Oct. 14; 16(38):4762-72.

Dyslipidemia

Dyslipidemia, or abnormal cholesterol and lipid homeostasis, is linked with prevalent diseases such as metabolic syndrome, atherosclerosis/cardiovascular disease, and type 2 diabetes. Cholesterol and lipids are trafficked in the blood as lipoprotein particles, such as low-density lipoprotein (LDL) and high-density lipoprotein (HDL) that ferry their fatty cargo to different cells and tissues. Excess circulating LDL can be oxidized and taken up by arterial macrophages, turning them into cholesterol/lipid-filled "foam cells" that are involved in the formation of atherosclerotic plaques. Triglycerides, as major components of very-low-density lipoprotein (VLDL), have been linked to atherosclerosis, and, by extension, the risk of heart disease and stroke. Elevated triglycerides (e.g., mildly elevated fasting levels, above 150 mg/dL (1.7 mmol/L), or high fasting levels above 200 mg/dL (2.26 mmol/L)) are common in subjects with metabolic syndrome/insulin resistance and those with poorly controlled diabetes, and contribute to the risk of atherosclerosis, heart disease, and stroke in that population. Increased stored triglycerides in tissues such as liver and white adipose tissue (WAT) are associated with non-alcoholic fatty liver disease and obesity, additional hallmarks of metabolic syndrome and insulin resistance.

In some embodiments, the dyslipidemia is elevated levels of serum triglycerides. Triglyceride (triacylglycerol, TAG or triacylglyceride) is an ester derived from glycerol and three fatty acids, and is the main constituent of vegetable oil and animal fats (Nelson, D. L.; Cox, M. M. *Lehninger, Principles of Biochemistry.* 3rd Ed. Worth Publishing: New York, 2000).

The American Heart Association has set guidelines for triglyceride levels (after fasting for 8-12 hours), as follows:

| Level (mg/dL) | Level (mmol/L) | Interpretation |
|---|---|---|
| <150 | <1.69 | Normal range, low risk |
| 150-199 | 1.70-2.25 | Borderline high |
| 200-499 | 2.26-5.65 | High |
| >500 | >5.65 | Very high: high risk |

Fasting triglyceride levels can be determined using any means known in the art, e.g., enzymatically using a glycerol kinase reaction-based colorimetric assay.

In some embodiments, the dyslipidemia is elevated levels of serum LDL Cholesterol. High levels of cholesterol increase risk of heart disease.

| LDL Cholesterol levels (mg/dL) | Levels (mmol/L) | LDL-Cholesterol Category |
|---|---|---|
| Less than 70 | Below 1.8 | Optimal for those at very high risk of heart disease |
| Less than 100 | Below 2.6 | Optimal |
| 100-129 | 2.6-3.3 | Near optimal/above optimal |
| 130-159 | 3.4-4.1 | Borderline high |
| 160-189 | 4.1-4.9 | High |
| 190 and above | Above 4.9 | Very high |

In some embodiments, the dyslipidemia is reduced levels of serum HDL Cholesterol. Lower levels of HDL cholesterol increase risk of heart disease, as HDL.

| HDL Cholesterol levels (mg/dL) | Levels (mmol/L) | HDL-Cholesterol Category |
|---|---|---|
| Below 40 (men) | Below 1 (men) | Poor |
| Below 50 (women) | Below 1.3 (women) | Poor |
| 50-59 | 1.3-1.5 | Better |
| 60 and above | Above 1.5 | Best |

In some embodiments, the dyslipidemia is elevated levels of Total Cholesterol. Total blood cholesterol is a measure of LDL cholesterol, HDL cholesterol, and other lipid components.

| Total Cholesterol levels (mg/dL) | Levels (mmol/L) | Total Cholesterol Category |
|---|---|---|
| Below 200 | Below 5.2 | Desirable |
| 200-239 | 5.2-6.2 | Borderline High |
| 240 and Above | Above 6.2 | High |

Plasma levels of HDL and LDL/VLDL are reciprocally related. Thus, a decrease in LDL would be reflected in an elevation of LDL/VLDL levels. A desirable treatment would be one that lowers LDL and raises LDL/VLDL; administration of a peptide described herein is expected to lower plasma triglycerides, total cholesterol, and LDL, and increase VLDL. In some embodiments, the methods include identifying a subject who has a dyslipidemia, e.g., elevated LDL, total cholesterol, or triglycerides, and/or decreased HDL and administering a therapeutically effective amount of a peptide as described herein. The methods can further include monitoring the subject, e.g., to determine efficacy of the peptide, by Obtaining one or more subsequent samples and determining a level of triglycerides in the subject. A decrease in triglyceride levels indicates that the peptide therapy was effective.

Diabetic and Pre-Diabetic Subjects

In some embodiments, the subjects treated by the methods described herein have diabetes, i.e., are diabetic. A person who is diabetic has one or more of a Fasting Plasma. Glucose Test result of 126 mg/dL or more; a 2-Hour Plasma Glucose Result in a Oral Glucose Tolerance Test of 200 mg/dL or more; and blood glucose level of 200 mg/dL or above. In some embodiments, the subjects treated by the methods described herein are being treated for diabetes, e.g., have been prescribed or are taking insulin, meglitinides, biguanides, thiazolidinediones, or alpha-glucosidase inhibitors.

in some embodiments the subjects are pre-diabetic, e.g., they have impaired glucose tolerance or impaired fasting glucose, e.g., as determined by standard clinical methods such as the intravenous glucose tolerance test (IVGTT) or oral glucose tolerance test (OGTT), e.g., a value of 7.8-11.0 mmol/t, two hours after a 75 g glucose drink for impaired glucose tolerance, or a fasting glucose level (e.g., before breakfast) of 6.1-6.9 mmol/L.

The pathogenesis of type 2 diabetes is believed to generally involve two core defects: insulin resistance and beta-cell failure (Martin et al., Lancet 340:925-929 (1992); Weyer et al., J. Clin. Invest. 104:787-794 (1999); DeFronzo et al., Diabetes Care. 15:318-368 (1992)). Important advances towards the understanding of the development of peripheral insulin resistance have been made in both animal models and humans (Bruning et al., Cell 88:561-572 (1997); Lauro et al., Nat. Genet, 20:294-298 (1998); Nandi et al. Physiol. Rev. 84:623-647 (200.4); Sreekumar et al., Diabetes 51:1913-1920 (2002); McCarthy and Froguel; Am. J. Physiol. Endocrinol.

Metab. 283:E217-E225 (2002); Mauvais-Jarvis and Kahn, Diabetes, Metab, 26:433-448 (2000); Petersen et al., N. Engl. J. Med. 350:664-671 (2004)). Thus, those subjects who have or are at risk for insulin resistance or impaired glucose tolerance are readily identifiable, and the treatment goals are well defined.

In some embodiments, the methods described herein include selecting subjects who have diabetes or pre-diabetes. In some embodiments, the following table is used to identify and/or select subjects who are diabetic or have pre-diabetes, i.e., impaired glucose tolerance and/or impaired fasting glucose.

| Fasting Blood Glucose | |
|---|---|
| From 70 to 99 mg/dL (3.9 to 5.5 mmol/L) | Normal fasting glucose |
| From 100 to 125 mg/dL (5.6 to 6.9 mmol/L) | Impaired fasting glucose (prediabetes) |
| 126 mg/dL (7.0 mmol/L) and above on more than one testing occasion | Diabetes |
| Oral Glucose Tolerance Test (OGTT) [except pregnancy] (2 hours after a 75-gram glucose drink) | |
| Less than 140 mg/dL (7.8 mmol/L) | Normal glucose tolerance |
| From 140 to 200 mg/dL (7.8 to 11.1 mmol/L) | Impaired glucose tolerance (prediabetes) |
| Over 200 mg/dL (11.1 mmol/L) on more than one testing occasion | Diabetes |

Body Mass Index (BMI)

Obesity increases a subject's risk of developing T2D. BMI is determined by weight relative to height, and equals a person's weight in kilograms divided by height in meters squared (BMI=kg/m$^2$). Accepted interpretations are given in Table 2.

TABLE 2

| Category | BMI |
|---|---|
| Underweight | ≤18.5 |
| Normal weight | 18.5-24.9 |
| Overweight | 25-29.9 |
| Obese | ≥30 |

Thus, the methods described herein can include determining a subject's height, determining a subject's weight, and calculating BMI from the values determined thereby. Alternatively, the methods described herein can include reviewing a subject's medical history to determine their BMI.

In some embodiments, the methods described herein include selecting subjects who have a BMI of 30 or above obese subjects).

Metabolic Syndrome

In some embodiments, the methods include determining whether a subject has the metabolic syndrome, and selecting the subject if they do have the metabolic syndrome, then administering a peptide as described herein. Determining whether a subject has the metabolic syndrome can include reviewing their medical history, or ordering or performing such tests as are necessary to establish a diagnosis.

The metabolic syndrome, initially termed Syndrome X (Reaven, Diabetes (1998) 37(12):1595-1607), refers to a clustering of obesity, dyslipidemia, non-alcoholic fatty liver disease, hypertension, and insulin resistance. All components of the metabolic syndrome are traditional risk factors for vascular disease. As used herein, the metabolic syndrome is defined by the presence of at least 3 of the following: abdominal obesity (excessive fat tissue in and around the abdomen, as measured by waist circumference: e.g., greater than 40 inches for men, and greater than 35 inches for women), fasting blood triglycerides (e.g., greater than or equal to 150 mg/dL), low blood HDL (e.g., less than 40 mg/dL for men, and less than 50 mg/dL for women), high blood pressure (e.g., greater than or equal to 130/85 mmHg) and/or elevated fasting glucose (e.g., greater than or equal to 110 mg/dL). In some embodiments, levels of these criteria may be higher or lower, depending on the subject; for example, in subjects of Asian ancestry; see, e.g., Meigs, Curr. Op. Endocrin. Diabetes, (2006) 13:103-110. A determination of the presence of metabolic syndrome can be made, e.g., by reviewing the subject's medical history, or by reviewing test results.

Based on data from the Third National Health and Nutrition Examination Survey (NHANES III) approximately 24% of the adults in the United States qualify as having the metabolic syndrome (Ford et al., JAMA. 287(3):356-359 (2002)). Insulin resistance is now felt to be central in the pathogenesis of these related disorders.

Dosage

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds ties preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a haft-maximal inhibition of symptoms) as determined in cell culture. Such information can be used to more accurately determine useful doses in humans. Levels in plasma may be measured, for example, high performance liquid chromatography.

Pharmaceutical Compositions and Methods of Administration

The methods described herein include the use of pharmaceutical compositions, that include GLP-1 C-terminal peptides described herein as active ingredients.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. As the nonapeptides described herein are the endproducts of neutral endopeptidase (neprilysin) actions, they are expected to be resistant to trypsin, chymotrypsin, and pepsin. Therefore the present invention includes an oral dosage form and methods that include oral administration of the nonapeptides.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories e.g., with conventional suppository bases such as cocoa butter and other glycerides) or retention enemas for rectal delivery.

In some embodiments, the GLP-1 C-terminal peptides are formulated with a cell penetrating agent as known in the art, e.g., liposomes or micelles. Biodegradable microparticle or nanoparticle delivery systems that increase intracellular uptake, e.g., polymeric and surface modified nanoparticles as described in US 2009/0136585 and can also be used. Examples include poly DL-lactide-co-glycolide (PLGA) nanoparticles, e.g., surface-modified with known surface-modifying agents, such as heparin, dodecylmethylammonium bromide (DMAB), DEAE-Dextran, lipofectin, and fibrinogen (see, e.g. Song et al., J. Control. Release, 54:201-

211 (1998); Labhasetwar et al., J. Pharm. Sci., 87:1229-1234 (1998); Lee et al., Biomaterials 29(9):1224-1232 (2008); and US 2009/0136585.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc, Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

EXAMPLES

The invention is further described in the following examples, which do not limit the scope of the invention described in the claims.

Example 1

GLP-1 (28-36)Amide Rapidly Enters Hepatocytes and Targets to Mitochondria Independently of the GLP-1 Receptor The peptide GLP-1(28-36)amide is reported to be a major end product of the selective proteolysis of GLP-1 by the neutral endopeptidase NEP 24.11 (Hupe-Sodmann et al. Regul. Pept. (1995)58:149-156) (FIG. 1). Since NEP 24.11 is an ubiquitous endopeptidase, and GLP-1(9-36) amide is reported to modulate cellular redox vasculature (Brownlee M. PCT/US2004/040852), and that cell respiration is a function carried out by mitochondria (Hirst J. Biochem J. (2009) 425:327-39), we examined the possibility that GLP-1(28-36) amide may gain access to hepatocytes and target to mitochondria.

GLP-1(28-36)amide (FIAWLVKGRamide (SEQ ID NO:1) and the GLP-1(28-37) Arg-34 glycine extended (FIAWLVRGRG (SEQ ID NO:4)) peptides were prepared by solid phase synthesis and purified by sequential HPLC to >98% single component homogeneity. Verification of the peptides was done by both amino acid composition analysis and by mass spectroscopy. Fluorescent-labeled GLP-1(28-36)amide was prepared with the green fluorescence compound, 5-carboxyfluorescein (5-FAM, fluorescein amidite) and added to hepatocytes isolated from the liver of an ob/ob mouse along with Mitotracker, a specific red fluorochrome mitochondrial marker from Molecular Probes (AnaSpec, Fremont Calif.). The mitotracker compound used requires oxidation to develop fluorescence emission and fluoresces only if cells are viable and actively respiring. The oxidized red fluorochrome stains mitochondria of live and poorly respiring cells (RedCMXRos #7512) and the reduced red fluorochrome stains only actively respiring cells (Red CM-H2XRos #7513).

Leptin-deficient ob/ob mice from 10-12 weeks of age were purchased from Jackson Laboratories (Bar Harbor, Me.). Diet induced obesity mice (DIO) were obtained after C57bl/6J mice of 10-12 weeks of age (purchased from Jackson Laboratories (Bar Harbor, Me.)) were fed a high-fat diet (60% kcal fat, Research Diets, Inc) for 9 weeks.

Mitochondrial localization was evaluated as follows, Hepatocytes were isolated from ob/ob mice and diet-induced obese (DIO) mice and plated overnight on 4 well glass slides (NUNC, Inc., IL) in maintenance medium (12), Next day cells were treated with 10 microM PAM-labeled GLP-1 (28-36)amide peptide (FAM-FIAWLVKGRamide (SEQ ID NO:1)) and 50 nM MitoTracker Red CM-H2Ros for 5 minutes in no dye, no PBS, 5 mM Glucose DMEM medium. Cells were washed with the same medium and images were taken 15 minutes later using Nikon Diaphot 300 inverted microscope SPOT RT camera and SPOT 3.3.1 software (Diagnostic Instruments, Inc., MI).

Hepatocytes were also isolated from DIO C57Bl/6J mice, plated as described above, and treated next day for 18 hours in 25 mM glucose maintenance medium with 5 microM GLP-1(28-36) and 500 nM MitoTrackerRed CM-H2XRos. Cells were washed and fixed with 70% methanol/30% acetone for 30 minutes at room temperature. Images were captured with Nikon Optiphot2 microscope using Photometric Coot Snap HQ camera (Photometrics, AZ) and IP Lab4.0 software (Scananlytics, Inc., VA).

Examination of the ob/ob mouse hepatocytes 15 min after addition of the compounds shows that the cellular distribution of GLP-1(28-36)amide (green) is indistinguishable from that of mitotracker suggesting that GLP-1(28-36)amide is targeting to mitochondria. The distribution of green fluorescent FAM-GLP-1(28-36)amide and red fluorescent Mitotracker observed in hepatocytes isolated from the diet-induced obese mouse was similar to that seen in the ob/ob mice.

Whether intracellular transport of FAM-GLP-1(28-36) amide is specific for CAT-1(28-36)amide was evaluated in hepatocytes isolated from Ob/Ob mice and treated for 18 hours with 1 microM Mitotracker Red CM-H2XRos and 1 microM of TAM labeled GLP-1 (28-36) peptide or irrelevant peptide controls: synapsin I-derived petide (FAM-LRRRIS-DANFamide (SEQ NO:13)), AnaSpec Cat #61756; IP3R-derived peptide (FAM-GRRESLTSFGamide (SEQ ID NO:14)), AnaSpec cat. #61731; or angiotensin I peptide (FAM-DRVYIHPFHL (SEQ ID NO:15)), AnaSpec cat. #61185, in 25 mM glucose maintenance medium. Irrelevant peptides were obtained from AnaSpec, Fremont, Calif. Celts were washed with 25 mM glucose Krebs-Ringer buffer. Images were taken using Nikon Diaphot 300 inverted microscope SPOT RT camera and SPOT 3.3.1 software (Diagnostic Instruments, Inc., MI). The three irrelevant FAM-peptides do not distribute in hepatocytes with the pattern of distribution of mitotracker, thus intracellular transport of FAM-GLP-1(28-36)amide appears to be specific for GLP-1(28-36)amide.

Whether transport of GLP-1(28-36)amide occurs by a mechanism independent of the GLP-1 receptor was next evaluated. Hepatocytes were isolated from ob/ob mouse and pretreated in 25 mM glucose Krebs-Ringer buffer for 2 hrs with 10 microM Exendin (9-39). 1 microM FAM labeled GLP-1 (28-36) and 500 nM MitoTrackerRed CM-H2XRos were added into the well and images taken 30 min later were compared to the images from wells where no exendin (9-39) was used for pretreatment.

That the transport of GLP-1(28-36)amide occurs by a mechanism(s) independent of the GLP-1 receptor is supported by the findings that the GLP-1 receptor antagonist, exendin(9-39) does not inhibit transport and that no binding of a fluorescence-labeled GLP-1, FAM-GLP-1, is detectable on the surface of isolated mouse hepatocytes, whereas a FAM-glucagon control hormone known to have receptors on hepatocytes readily binds to the surface of hepatocytes. Based on these collective observations we conclude that the transport of GLP-1(28-36)amide into hepatocytes is relatively specific, occurs by GLP-1 receptor-independent mechanisms, and is targeting to mitochondria in the hepatocytes.

Example 2

GLP-1(28-36)Amide Inhibits Glucose Production in Isolated Mouse Hepatocytes

To determine whether there may be effects of GLP-1(28-36)amide on mitochondrial functions of oxidative phosphorylation hepatocytes, gluconeogenesis was examined because uncontrolled hepatic gluconeogenesis is an important contributors to fasting hyperglycemia in insulin-resistant diabetic individuals. Gluconeogenesis was stimulated in the isolated mouse hepatocytes by the addition of cAMP, dexamethasone, and lactate as described earlier (Tomas et al. Horm. Metab. Res. (2010) 42:657-662; Liu et al. J Biol. Chem. (2007) 282:14205-14212), Glucose production assays were performed as follows. Primary hepatocytes ($2 \times 10^5$ cells per well in twelve-well plates) were pre-treated with GLP-1(28-36)amide for 1 hour followed by stimulation with cAMP (10 microM)/dexamethasone (50 mM)/sodium lactate (2 mM) in glucose-free DMEM without phenol red. The culture media were collected for measuring glucose concentration with a colorimetric glucose assay kit (Sigma). The readings were then normalized to total protein content determined from whole-cell lysates.

Figure 2:
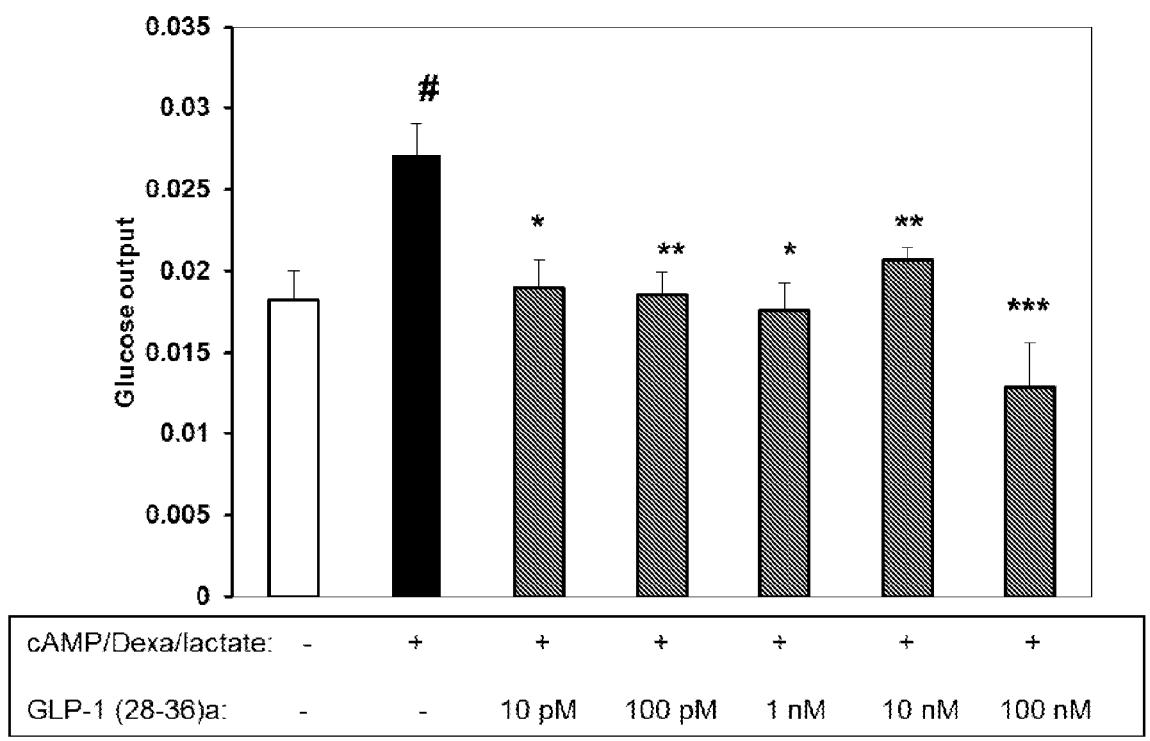
FIG. 2 is a bar graph showing a composite of four independent experiments showing dose-dependent inhibition of glucose production augmented by the gluconeogenic cocktail (gng) consisting of cyclicAMP (cAMP), dexamethasone (Dexa), and lactate. Cells were pretreated with GLP-1(28-36) amide at indicated concentrations in serum free DMEM for 1 h, and then treated for 2.5 h with cAMP (10 microM) and Dexamethasome (50 nM) in serum- and glucose-free DMEM supplemented with 2 mM sodium lactate in the continued presence of GLP-1(28-36)amide. Readings were normalized to protein concentration. Results presented represent mean±S.E of four independent experiments, each in duplicate. #p<8E-04 gng vs (−) n=31. (*) p<0.01 gng vs 10 pM n=12. (**) p<0.005 gng vs 100 pM n=13. (*) p<0.002 gng vs 1 nM n=14. () p<0.046 gng vs 10 nM n=9. (*) p<0.004 gng vs 100 nM n=5

The addition of GLP-1(28-36)amide to the hepatocytes dose-dependently suppressed glucose formation (FIG. 2).

Example 3

GLP-1(28-36)Amide Enhances ATP Levels and Suppresses Oxidative Stress and ROS Formation in Isolated Mouse Hepatocytes Because the production of reactive oxygen species (ROS) by mitochondria is believed to be a major trigger for the development of insulin resistance (Haas et al. Curr Opin Lipidol. (2009) 20:206-10), hepatic steatosis (Grattagliano et al. J Nutr Biochem. (2008) 19:491-504), and apoptosis via the stimulation of cytochrome C release and the activation of the caspase cascade (Ott et al. Apoptosis. (2007) 12:913-922), the intracellular levels of ATP and reactive oxygen species (ROS) were measured in hepatocytes in response to GLP-1(28-36) amide (FIGS. 3A-C). ATP levels were determined by the ATPlite luminescence assay as follows. Primary hepatocytes and H4IIe cells were plated in 96-well plates at a density of 1×104/well and treated with tert-butyryl hydroperoxide (tBHP) (0.5 mM) and H2O2 (0.7-1.0 mM) for 1 hour and overnight respectively in the presence or absence of GLP-1 (28-36)amide (100 nM). H4IIe cells were allowed to grow for 2 days before treatment. ATP levels were assessed by a ATPlite one-step luminescence ATP detection assay system (PerkinElmer, Waltham, Mass.). The hepatocyte cell line H4IIe (FIG. 3A) and hepatocytes isolated from the livers of diet-induced obese (DIO) mice (FIG. 3B) were pre-treated with GLP-1(28-36)amide or vehicle control.

Figure 3D:
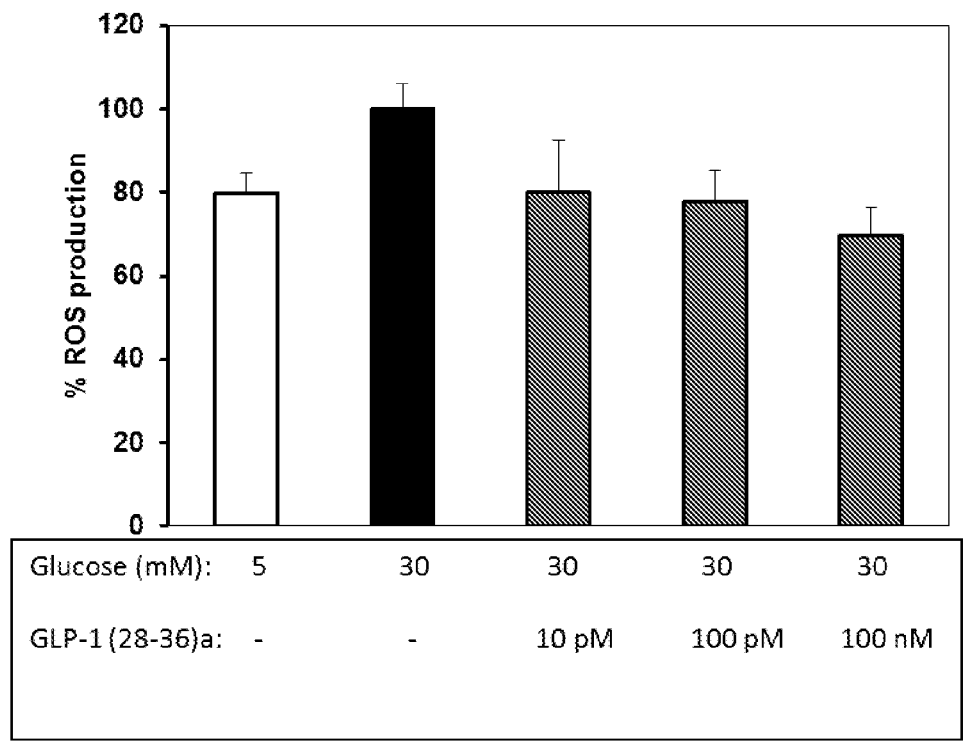
FIG. 3D is a bar graph showing that suppression of ROS production by nonapeptide GLP-1(28-36)a in 30 mM glucose-stimulated hepatocytes isolated from 12-19 week old mice was dose-dependent.

Oxidative stress was augmented by the addition of either tert-butyryl hydroperoxide (tBHP) for one hour or hydrogen peroxide ($H_2O_2$) overnight. Oxidative stress impairs mitochondrial functions, including generation of ATP, and reduces cell viability. ROS formation assays were performed as follows. Primary hepatocytes from diet induced obesity (DIO) and C57BL/6J mice were plated in 96-well plates at a density of 1×104/well for 24 h before overnight treatment with GLP-1(28-36)amide followed by tBHP (0.5 mM) for 1 hour. Intracellular ROS was measured by 5-(and 6)-carboxy-2',7'-dichlorohydro-fluorescein diacetate (Molecular Probes, Eugene, Oreg.). The treatment of the cells with GLP-1(28-36)amide protected both DIO hepatocytes and H4IIe cells against the fall in ATP levels induced by tBHP or $H_2O_2$ (FIGS. 3A-B). In addition to ATP levels ROS levels were measured in hepatocytes using the fluorescent indicator $CMH_2DCFDA$. Treatment of the hepatocytes isolated from DIO mice and normal mice (C57bl/6J) with GLP-1(28-36)amide lowered cellular ROS levels both at basal conditions and after elevation of ROS levels in response to the addition of tBHP, and inducer of oxidative stress (Zhao et al. J. Biol. Chem. (2004); 279:34682-90) (FIG. 3C). The suppression of ROS production by nonapeptide GLP-1(28-36)a isolated 30 mM-stimulated hepatocytes was dose-dependent (FIG. 3D).

Example 4

GLP-1(28-36)Amide Infusions Result in an Inhibition of Triglyceride Accumulation in the Livers of High Fat Fed Mice GLP-1(28-36)amide, FIAWLVKGRamide (SEQ ID NO:1), was prepared by solid phase peptide synthesis in the MGH Biopolymers Core Laboratory. The peptide was >98% valid peptide by HPLC and mass spectrometry analyses. Osmotic pumps (Alzet #1004 osmopumps) were from Alzet. Other reagents were from Sigma-Aldrich.

Male C57bl/6 mice at 6 or 10 weeks of age were placed on a very high fat diet (VHFD, 60% fat, Research Diets) for 4 to 7 weeks. At 10 to 17 weeks of age mini-osmopumps containing either vehicle or GLP-1(28-36)amide were implanted subcutaneously for delivery of peptide or vehicle over 3 to 11 weeks. Twenty nanomoles of peptide (in 0.9% NaCl containing 0.1% human serum albumin) was infused at a rate of 18.5 nanomoles/KgBW/day for 3 to 11 weeks to achieve an estimated concentration of approximately 100 pM similar to that reported by infusions of GLP-1(7-36) amide (Zhang et al., Diabetologia. (2007); 50:1900-1999). For infusions longer than 4 weeks additional osmopumps with peptide were implanted at the end of each 4 weeks infusion. Body weights were recorded weekly. Food consumption was assessed every 3 to 4 days by weight. Energy intake (Kcal/gm body weight/week) and Feed Efficiency Index (FEI) was evaluated during the infusions of vehicle or peptide. The latter provides a measure of the efficiency of caloric conversion to body weight and it is calculated by determining the grams of body weight gain per cage/Kcal of food consumed per cage, (Parekh et al., Metabolism. (1998); 47: 1089-1096). There was no observable change in the activities of the mice amongst the various experimental groups. Mice did not show any change in activity amongst the various experimental groups.

Analyses of liver sections for lipid accumulation and triglyceride content were performed as follows. Paraffin embedded sections of liver were stained with H & E and evaluated for fat content by absence of staining. Liver triglycerides were extracted and measured using a colorimetric enzymatic assay (Serum Triglyceride Determination kit, Sigma).

Figure 4A:
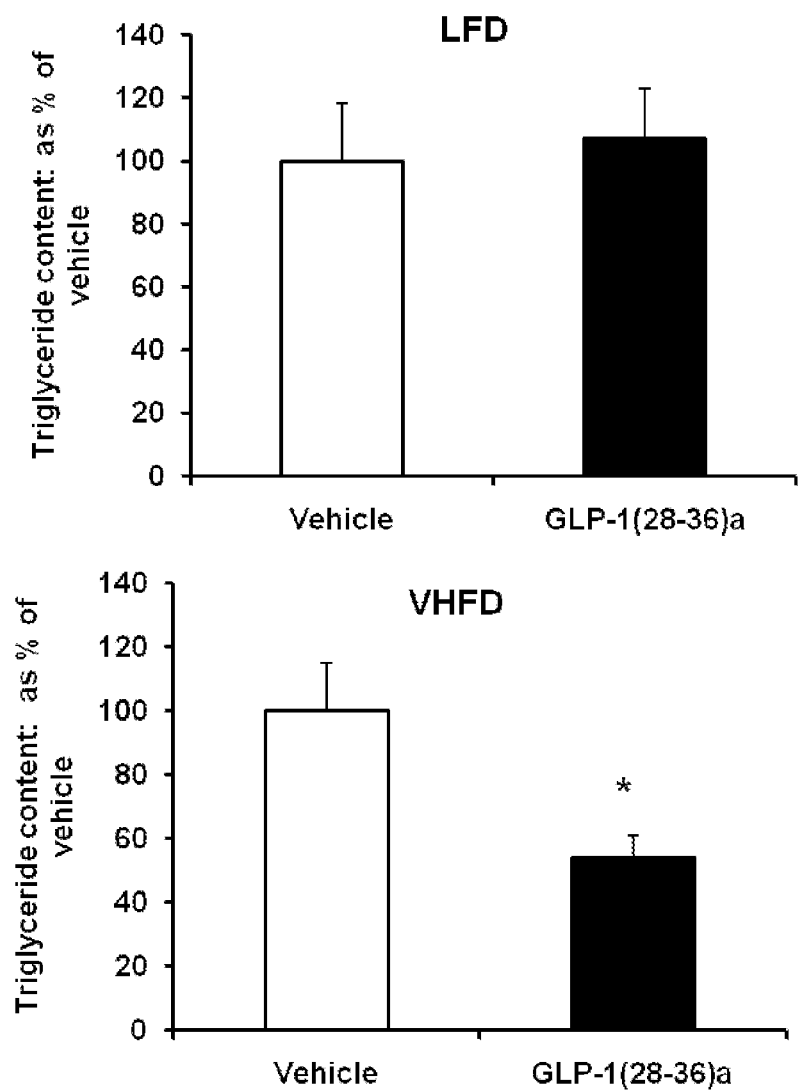
FIG. 4A is a pair of bar graphs showing triglyceride contents of samples of livers of mice fed a low fat diet (LFD, upper panel) or very high fat diet (VHFD, lower panel) after 3 to 8 weeks peptide infusions. Values are represented as % of vehicle control in mice fed in LFD and VHFD. *p<0.02, peptide vs. vehicle.

Livers from mice fed the control LFD and infused with GLP-1(28-36)amide were not different from mice infused with vehicle alone. However, livers from mice fed VHFD and receiving infusions of vehicle developed steatosis and the infusion of GLP-1(28-36)amide prevented or reversed the steatotic phenotype. These findings were corroborated by staining of sections of liver with hematoxylin and eosin in which fat deposition (no staining) was higher in mice fed VHFD compared to control LFD and the infusion of GLP-1 (28-36)amide substantially diminished the amount of fat deposited in sections of the livers of the VHFD mice. Likewise, triglyceride content in the livers of mice fed LFD and infused with GLP-1(28-36)amide were no different from those infused with control vehicle (FIG. 4A). The infusion of GLP-1(28-36)amide to mice fed the VHFD diminished the triglyceride accumulation by 40% compared to control vehicle infusion (FIG. 4A).

Figure 4B:
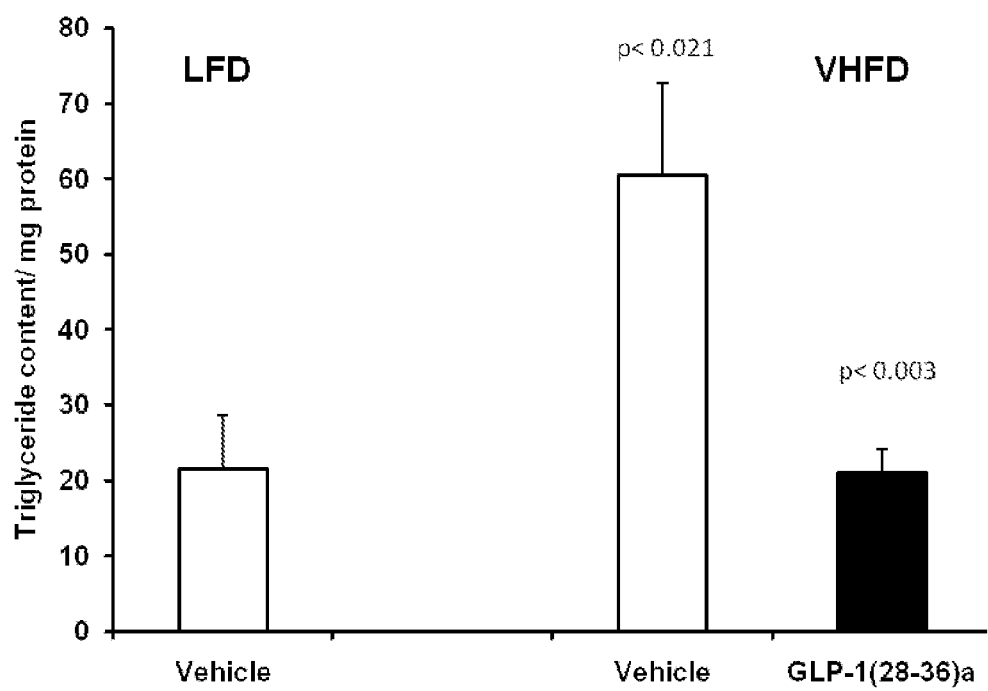
FIG. 4B is a bar graph showing triglyceride contents of samples of livers of mice fed a low fat diet (LFD) or very high fat diet (VHFD), per mg of protein.
Figure 4C:
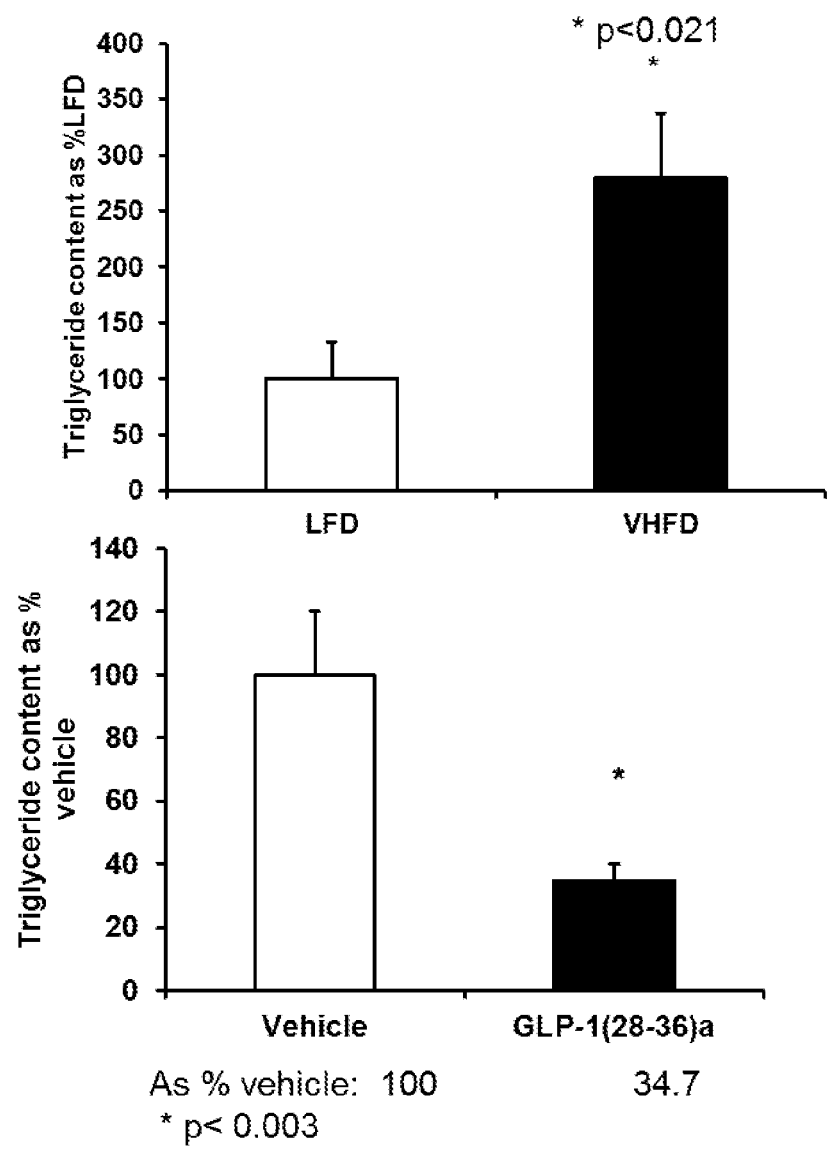
FIG. 4C is a pair of bar graphs showing triglyceride contents of samples of livers of mice fed a low fat diet (LFD) or very high fat diet (VHFD) after peptide infusions. Values are represented as % of LFD (Upper panel) or % of vehicle control in mice fed in VHFD (lower panel).

Similar experiments were performed in which the mini osmopumps were implanted at 23 weeks of age, and 17 weeks on diet. The results, presented in FIGS. 4B-C, were similar even in this older, more obese group of mice, and showed that triglyceride content in the livers of mice fed VHFD and infused with GLP-1(28-36)amide were reduced to levels similar to levels in mice fed a LFD (LFD: 21.6±7; VHFD (Vehicle): 60.5±12.1; VHFD (GLP-1 (28-36)a): 21.02±3.1); FIG. 4B. Levels in animals fed VHFD and infused with GLP-1 (28-36)amide were about a third of those infused with vehicle (FIG. 4C). These studies show that infusion of GLP-1(28-36)amide reverses steatosis in obese mice fed the VHFD for 17 weeks prior to the beginning of the peptide infusions. The liver triglyceride levels in the livers of the mice receiving the peptide infusion are not different from the levels in normal mice fed the LFD, whereas the livers of control obese mice fed the VHFD and receiving the control vehicle-only without peptide have fatty livers in which triglyceride levels are elevated by 3-fold above the levels in normal LFD-fed mice and obese VHFD-fed receiving the inert control vehicle.

Example 5

GLP-1(28-36)Amide Attenuates Weight Gain in High Fat-Fed Mice

In additional experiments, male C57bl/6 mice at 6 or 10 weeks of age were placed on a very high fat diet (VHFD, 60% fat, Research Diets) for 4-7 weeks. At 10-17 weeks of age mini-osmopumps containing either vehicle or GLP-1(28-36) amide were implanted subcutaneously for delivery of peptide or vehicle over 3-11 weeks. Twenty nanomoles of GLP-1(28-36)amide was diluted in either saline containing 0.1% human serum albumin (solvent 1) or in 20% acetic acid in saline containing a final concentration of 0.08% human serum albumin (solvent 2), and were infused at a rate of 18.5 nanomoles/kg BW/day for 3-11 weeks to achieve an estimated concentration of approximately 100 pM similar to that reported by infusions of GLP-1(7-36) amide (Zhang et al., Diabetologia (2007); 50:1900-99). For infusions longer than 4 weeks additional osmopumps with peptide were implanted at the end of each 4 weeks infusion. Body weights were recorded weekly, Food consumption was assessed every 3-4 days by weight Energy intake (kcal/g BW/week) and feed efficiency index (FEI) was evaluated during the infusions of vehicle or peptide. The latter provides a measure of the efficiency of caloric conversion to bodyweight and it is calculated by determining the grams of body weight gain per cage/kcal of food consumed per cage (Parekh et al., Metabolism (1998); 47:1089-96). There was no observable change in the activities of the mice amongst the various experimental groups.

Figure 5A:
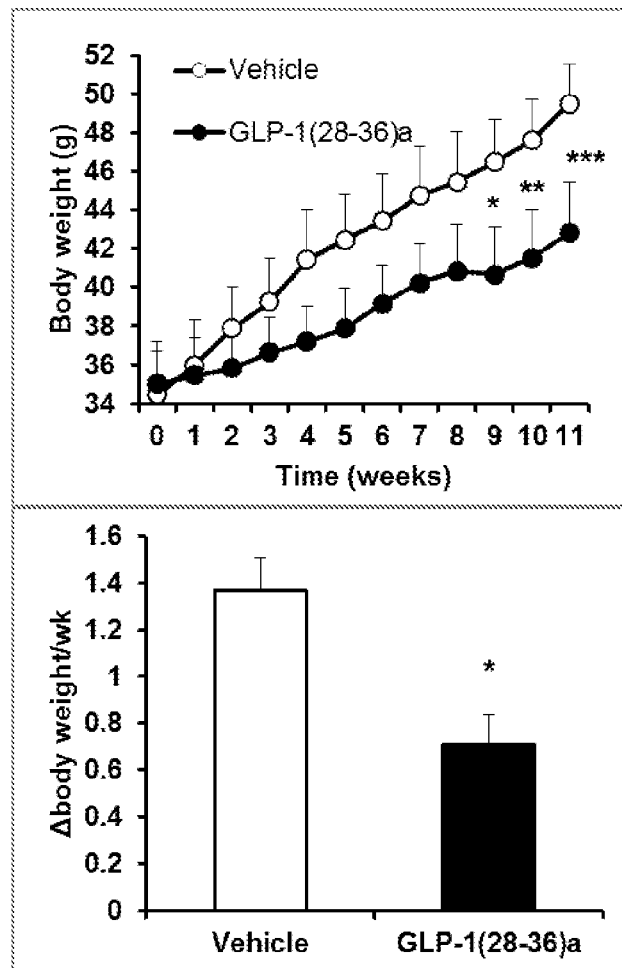
FIG. 5A is a line graph and a bar graph showing curtailment of weight gain in mice fed a VHFD in response to 11-week infusions of GLP-1(28-36)amide. Left panel: Body weights were measured weekly. Highly significant differences in weights at weeks 9-11. *p<0.05, p,0.045, *p<0.028 peptide vs. vehicle, Right panel: Weekly incremental mean changes in body weights of data shown in left panel, *p<0.001 peptide vs. vehicle.

The infusion of GLP-1(28-36)amide for 11 weeks curtailed the rate of weight gain in mice fed VHFD (FIG. 5A). The inhibition of weight gain reached statistical significance by week 9 and it was maintained until the end of the 11 weeks infusion. In addition, the average change in body weight gain per week of mice receiving peptide was 50% less than that of the mice receiving control vehicle, Likewise, a short term infusion of GLP-1(28-36)amide for 3 weeks inhibited weight gain in mice fed a VHD but no effects of the infusion of GLP-1(28-36)amide on weight gain were seen in mice fed the control LFD.

Figure 5B:
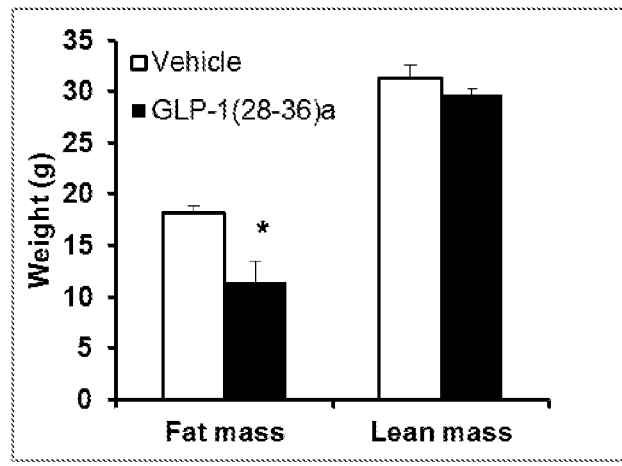
FIG. 5B is a bar graph showing fat and lean mass of mice in (5A) after 11 weeks of infusions of peptide or vehicle. Fat and lean mass measurements were made by dual emission X-ray absorptiometry (DXA). *p<0.01
Figure 5C:
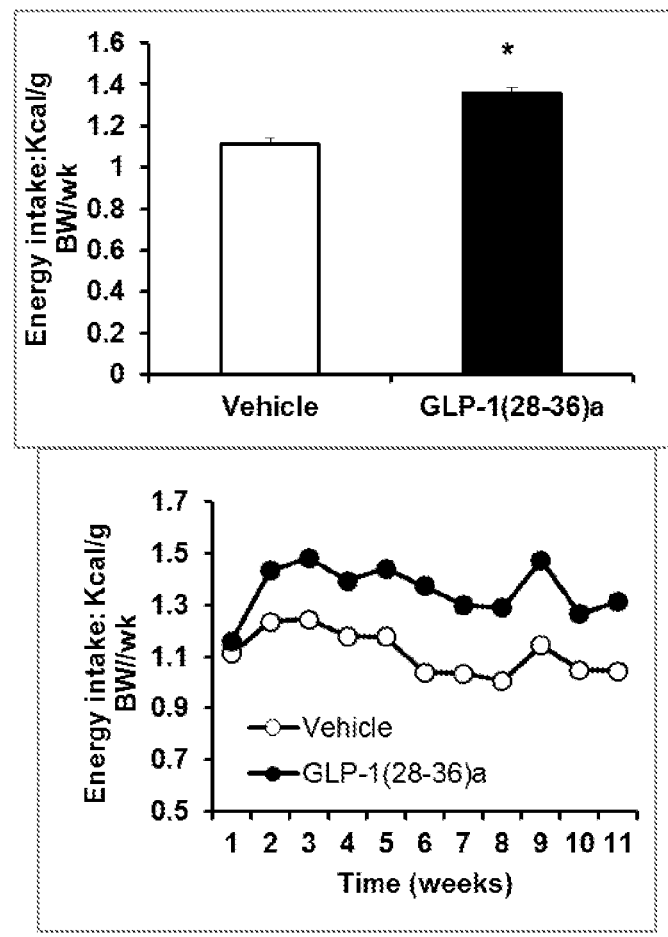
FIG. 5C is a line graph and a bar graph showing energy intake of mice receiving 11-week infusions of vehicle or GLP-1(28-36)amide. Left panel: Energy intake in kcal/g BW/week. Right panel: Mean energy intakes per week for 11 weeks of data shown in left panel. *p<3.04E-06, peptide vs. vehicle.
Figure 5D:
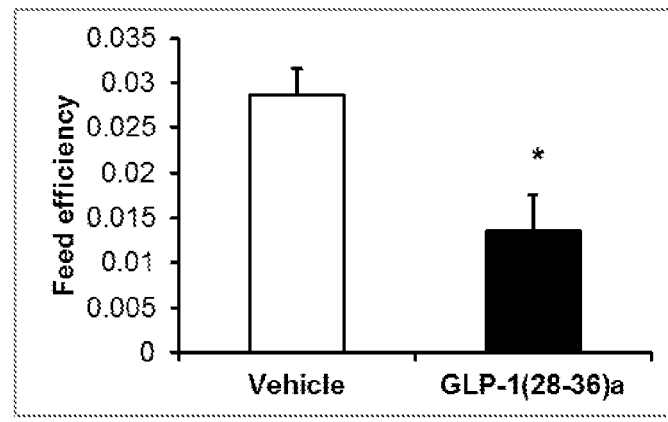
FIG. 5D is a bar graph showing feed efficiency index of mice in (5C). *p<2.9E-04, peptide vs. vehicle.

Measurements of body lean and fat mass were made at week 11 by Dual energy X-ray absorptiometry (DXA) as follows, Mice were anesthetized with 0.02 ml of a 2% tribromoethanol solution per gram of body weight and scanned with a dual X-ray apparatus (Lunar Piximus, GE Medical Systems, Wauwatosa, Wis.), Total, fat, and lean body mass was quantitatively determined. The results showed a 37% reduction in fat mass in the peptide-infused mice compared to control mice and no significant changes in lean mass (FIG. 5B).

Similar results were obtained in experiments performed in which the mini osmopumps were implanted at 23 weeks of age, and 17 weeks on diet.

Example 6

GLP-1(28-36)Amide Corrects Dyslipidemia in High Fat-Fed Mice

In additional experiments, male C57bl/6 mice at 6 or 10 weeks of age are placed on a very high fat diet (VHFD, 60% fat, ResearchDiets) for 4-7 weeks. At 10-23 weeks of age mini-osmopumps containing either vehicle or GLP-1(28-36) amide are implanted subcutaneously for delivery of peptide or vehicle over 3-11 weeks, Twenty nanomoles of GLP-1(28-36)amide are diluted in either saline containing 0.1% human serum albumin (solvent 1) or in 20% acetic acid in saline containing a final concentration of 0.08% human serum albumin (solvent 2), and are infused at a rate of 18.5 nanomoles/kg BW/day for 3-11 weeks to achieve an estimated concentration of approximately 100 pM similar to that reported by infusions of GLP-1(7-36) amide (Zhang et al., Diabetologia (2007) 50:1900-99). For infusions longer than 4 weeks additional osmopumps with peptide are implanted at the end of each 4 weeks infusion. Body weights are recorded weekly. Food consumption is assessed every 3-4 days by weight. Energy intake (kcal/g BW/week) and feed efficiency index (FED are evaluated during the infusions of vehicle or peptide. Blood lipid levels, including HDL, LDL, total cholesterol, and triglyceride levels, are measured using known methods, e.g., HPLC or LC/MS. Because dyslipidemia is a precursor to steatosis, it is expected that the animals will display dyslipidemia before treatment with the peptide, and that the dyslipidemia will be ameliorated during the course of treatment.

Example 7

Oral Administration of GLP-1(28-36)Amide

This example describes experiments to demonstrate oral availability of GLP-1(28-36)amide, 150 micrograms of the GLP-1(28-36)amide are administered by oral gavage to adult mice (~30 gms BW), e.g., DIO, ob/ob, or db/db mice, by giving a solution including 0.15 ml of a 1.0 mg/ml solution of 28-36 in 10 mM sodium acetate, pH 4.0/0.1% HSA/saline (prepared by dissolving 2.0 mg (1.0 mg peptide) in 1 ml 10 mM sodium acetate pH 4.0/0.1% HSA/saline=1.0 mg/ml), and optionally 0.05 ml of sucrose syrup to prepare a sweetened solution (when used, total volume=0.20 ml). The gavage volume limit is about 10 ml/Kg BW.

Blood, e.g., 0.5 to 1.0 ml, is collected by tail snip at 15 min and 30 min. Tail snip is preferred over tail nick to obtain sufficient blood. Blood is collected in EDTA tubes to obtain plasma.

Oral absorption typically gives 10% bioavailability as compared to IV administration. SubQ is 30% and IP 50%. Thus, the oral dose will be 5× more than is given IP. Gavage dose=150 microgams in 0.15 ml. The MCR of the peptide is likely to be about 40-50 ml/min. Based on these estimations, the plasma levels of peptide achieved should be in the range of 100 to 200 pM.

References

[1] Lovshin, JA and Drucker, D J. Incretin-based therapies for type 2 diabetes mellitus. Nat. Rev. Endocrinol. 2009; 5:262-9.

[2] Kieffer, T. J. and Habener, J. F. The glucagon-like peptides. Endocr Rev. 1999; 20:876-913.

[3] Hansen L, Deacon C F, Orskov C, Holst J J. Glucagon-like peptide-1-(7-36)amide is transformed to glucagon-like peptide-1-(9-36) amide by dipeptidyl peptidase IV in the capillaries supplying the L cells of the porcine intestine. Endocrinology. 1999; 140:5356-63.

[4] Ban, K, Noyan-Ashraf, MH, Hoefer, J, Bolz, SS, Drucker, DJ, Husain, M. Cardioprotective and vasodilatory actions of glucagon-like peptide 1 receptor are mediated through both glucagon-like peptide 1 receptor-dependent and -independent pathways, Circulation 2008; 117:2340-50.

[5] Sonne, D. P., Engstrøm, Y T., Treiman, M. Protective effects of GLP-1 analogues exendin-4 and GLP-1(9-36) amide against ischemia-reperfusion injury in rat heart. Regul. Pept. 2008; 146: 243-9,

[6] Nikolaidis, LA, Elahi D, Shen, YT, Shannon, RP. Active metabolite of GLP-1 mediates myocardial glucose uptake and improves left ventricular performance in conscious dogs with dilated cardiomyopathy. Am. J. Physiol. Heart Circ. Physiol. 2005; 289:H2401-H2408.

[7] Ban K, Kim K H, Cho C K, Sauvé M, Diamandis E P, Backx P H, Drucker D J, Husain M. Glucagon-like peptide (GLP)-1(9-36)amide-mediated cytoprotection is blocked by exendin(9-39) yet does not require the known GLP-1 receptor. Endocrinology. 2010; 151:1520-31.

[8] Green, BD, Hand, K V, Dougan, JE, McDonnell, BM, Cassidy, RS, Grieve, DJ. GLP-1 and related peptides cause concentration-dependent relaxation of rat aorta through a pathway involving KATP and cAMP. Arch. Biochem, Biophys, 2008; 478:136-42.

[9] Elahi, D. Egan, JM, Shannon, RP, Meneilly, GS, Khatri, A, Habener, JF, Andersen, DK. Glucagon-like peptide-1 (9-36)amide, cleavage product of glucagon-like peptide-1 (7-36) is a glucoregulatory peptide. Obesity 2008; 16:1501-9.

[10] Abu-Hamdah, R, Rabiee, A, Meneilly, OS, Shannon, RP, Andersen, DK, Elahi D, Clinical review: The extrapancreatic effects of glucagon-like peptide-1 and related peptides. J. Clin. Endocrinol Metab. 2009; 94:1843-52.

[11] Tomas E, Habener J F. Insulin-like actions of glucagon-like peptide-1: A dual receptor hypothesis. Trends Endocrinol Metab 2010; 21:59-67.

[12] Tomas E, Stanojevic V, Habener, JR GLP-1(9-36) amide metabolite suppression of glucose production in isolated mouse hepatocytes. Horm. Metab, Res. 2010; 42(9): 657-662.

[13] Meier J J, Gethmann A, Nauck M A, Gotze O, Schmitz F, Deacon C F, Gallwitz B, Schmidt W E, Holst J J The glucagon-like peptide-1 metabolite GLP-1-(9-36) amide reduces postprandial glycemia independently of gastric emptying and insulin secretion in humans. Am J Physiol Endocrinol Metab 2006; 290:E1118-E1123.

[14] Deacon C F. Circulation and degradation of GIP and GLP-1. Horm. Metab. Res. 2004; 36:761-5.

[15] Plamboeck, A., Hoist, J. J., Carr, R. D., Deacon, C. F. Neutral endopeptidase 24.11 and dipeptidyl peptidase IV are both mediators of the degradation of glucagon-like peptide 1 in the anaesthetised pig. Diabetologia. 2005; 48:1882-90.

[16] Simonsen L, Pilgaard S, Carr R D, Kanstrup A B, Holst J J, Deacon C F. Inhibition of neutral endopeptidase 24.11 does not potentiate the improvement in glycemic control obtained with dipeptidyl peptidase-4 inhibition in diabetic Goto-Kakizaki rats. Horm. Metab, Res. 2009; 41:851-3,

[17] Flock, G, Baggio, L. L., Longuet, C., Drucker, J. J. (2007) Incretin receptors for glucagon-like peptide 1 and glucose-dependent insulinotropic polypeptide are essential for the sustained metabolic actions of vildagliptin in mice. Diabetes 2007; 56: 3006-13.

[18] Brun C, Philip-Couderc P, Raggenbass M, Roatti A, Baertschi A J. Intracellular targeting of truncated secretory peptides in the mammalian heart and brain, FASEB J 2006; 20:732-4.

[19] Yamada, H., Chounan, R., Higashi, Y., Kurihara, N., Kido, H. Mitochondrial targeting sequence of the influenza A virus PB1-F2 protein and its function in mitochondria. FEBS Lett. 2004; 578:331-6.

[20] Lemire B D, Frankenhauser C, Baker A, Schatz Z. The mitochondrial targeting function of randomly generated peptide sequences correlates with predicted helical amphiphilicity. J. Biol. Chem. 1989; 264:20205-15.

[21] Chatre L, Matheson L A, Jack A S, Hanton S L, Brandizzi F. Efficient mitochondrial targeting relies on co-operation of multiple protein signals in plants. J Exp Bot, 2009; 60:741-49,

[22] Baldwin G S. Antiproliferative gastrin/cholecystokinin receptor antagonists target the 78-kDa gastrin-binding protein. Proc Natl Acad Sci USA. 1994; 91:7593-97.

[23] Hashimoto T, Shindo Y, Souri M, Baldwin G S. A new inhibitor of mitochondrial, fatty acid oxidation, J. Biochem. 1996; 119:1196-201,

[24] Rodrigue-Way A, Demers A, Ong H, Tremblay A. A growth hormone-releasing peptide promotes mitochondrial biogenesis and a fat burning-like phenotype through scavenger receptor CD36 in white adipocytes. Endocrinology. 2007; 148:1009-18.

[25] Randle P J. Regulatory interactions between lipids and carbohydrates: the glucose fatty acid cycle after 35 years. Diabetes Metab Rev 1998; 14:263-83.

[26] Stein L L, Dong M H, Loomba R. Insulin sensitizers in nonalcoholic fatty liver disease and steatohepatitis: Current status. Adv Ther, 2009; 26:893-907.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating or preventing a dyslipidemia or a fatty liver disease (FLD) in a mammal, the method comprising administering to the mammal a therapeutically effective amount of a peptide consisting of (Phe/Tyr)-Ile-Ala-Trp-Leu-Val-(Lys/Arg)-Gly-Arg-Xaa (SEQ ID NO:9), wherein Xaa can be Gly, Gly-Arg, Gly-Arg-Gly, or absent, wherein one or more amino acid residues of SEQ ID NO:9 are modified by attachment of a fatty acid.

2. The method of claim 1, wherein the peptide is amidated, acetylated, or both.

3. The method of claim 1, wherein the fatty acid is selected from the group consisting of palmitate and oleate.

4. The method of claim 1, wherein the peptide consists of SEQ ID NO:1.

5. The method of claim 4, wherein the peptide is amidated, acetylated, or both.

6. The method of claim 4, wherein the fatty acid is selected from the group consisting of palmitate and oleate.

7. The method of claim 1, wherein the mammal has Non-alcoholic Steatohepatitis (NASH) or is at risk of developing NASH.

8. The method of claim 1, wherein the mammal has Non-alcoholic Fatty Liver Disease (NAFLD) or is at risk of developing NAFLD.

9. The method of claim 1, further comprising selecting the mammal on the basis that they have or are at risk of developing a FLD.

10. The method of claim 1, further comprising evaluating fatty liver disease in the subject, before, during, or after administration of the peptide.

11. The method of claim 1, wherein the subject has elevated levels of total cholesterol, high-density lipoprotein (HDL), or triglycerides compared to normal ranges of total cholesterol, HDL, or triglyceride level respectively in healthy subjects.

12. The method of claim 1, wherein the peptide is administered orally.

* * * * *